United States Patent [19]
Czech et al.

[11] Patent Number: 5,989,893
[45] Date of Patent: Nov. 23, 1999

[54] RECEPTOR-ACTIVATED REPORTER SYSTEMS

[75] Inventors: Michael P. Czech; Silvia Corvera, both of Wrentham, Mass.

[73] Assignee: University of Massachusetts Medical Center, Worcester, Mass.

[21] Appl. No.: 08/287,537

[22] Filed: Aug. 8, 1994

Related U.S. Application Data

[63] Continuation-in-part of application No. 08/127,316, Sep. 27, 1993, abandoned.

[51] Int. Cl.$^6$ .................................................. C12N 1/21
[52] U.S. Cl. .................. 435/252.3; 435/69.1; 435/320.1; 435/69.7; 536/23.1; 536/23.5; 536/23.4
[58] Field of Search .............................. 435/320.1, 240.2, 435/252.3, 69.7, 69.1, 7.2, 7.7, 7.1; 536/23.4, 23.5, 23.1

[56] References Cited

FOREIGN PATENT DOCUMENTS

| | | |
|---|---|---|
| 0 244 221 | 11/1987 | European Pat. Off. . |
| 0 366 238 | 5/1990 | European Pat. Off. . |
| WO 91/03554 | 3/1991 | WIPO . |
| PCT/US94/ 10936 | 1/1995 | WIPO . |

OTHER PUBLICATIONS

Calamia et al. (1990) Proc. Natl. Acad. Sci. USA 87, pp. 4937–4941, 1990.
Olson et al. (1993) J. Biol. Chem. 268/13, pp. 9839–9846, 1993.
Fukumoto et al., Journal of Biological Chemistry, vol. 264, No. 14, 1989, pp. 7776–7779.
Harrison et al., Journal of Biological Chemistry, vol. 267, No. 6, 1992, pp. 3783–3788.
Database WPI, Week 9106, Derwent Publications Ltd., London, GB; AN 91–041061 & JP, A,2 308 791, Dec. 21, 1990 Abstract.
Asano et al., Domains Responsible for the Differential Targeting of Glucose Transporter Isoforms, J. Biol. Chem. 267:19636–19641, 1992.
Czech and Buxton, Insulin Action on the Internalization of the GLUT4 Glucose Transporter in Isolated Rat Adipocytes, J. Biol. Chem. 268:9187–9190, 1993.
Czech et al., Exofacial Epitope–tagged Glucose Transporter Chimeras Reveal COOH–Terminal Sequences Governing Cellular Localization, J. Cell Biol. 123;127–135, 1993.
Czech et al., Complex Regulation of Simple Sugar Transport in Insulin–Responsive Cells, Trends Biochem. Sci. 17:197–201, 1992.

Hudson et al., Targeting of the "Insulin–responsive" Glucose Trasporter (GLUT4) to the Regulated Secretory Pathway in PC12 Cells, J. Cell Biol. 122:579–588, 1993.
Johnson et al., A His–Leu–Leu Sequence near the Carboxyl Terminus of the Cytoplasmic Domain of the Cation–dependent . . . Necessary for the Lysosomal Enzyme Sorting Function, J. Biol. Chem. 267:17110–17115, 1992.
Johnson et al., The Cytoplasmic Tail of the Mannose 6–Phosphate/Insulin–Like Growth Factor–II Receptor has Two Signals for Lysosomal Enzyme Sorting in the GoLgi, J. Cell Biol. 119:249–257, 1992.
Jhun et al., Effects of Insulin on Steady State Kinetics of GLUT4 Subcellular Distribution in Rat Adipocytes J. Biol. Chem. 267:17710–17715, 1992.
Kanai et al., Direct Demonstration of Insulin–Induced GLUT4 Translocation to the Surface of Intact Cells by Insertion of a c–myc Epitope into an Exofacial GLUT4 Domain, J. Biol. Chem. 268:14523–14526, 1993.
Letourneur et al., A Novel Di–Leucine Motif and a Tyrosine–Based Motif Independently Mediate Lysosomal Targeting and Endocytosis of CD3 Chains, Cell 69:1143–1157, 1992.
Marshall et al., Domains that Confer Intracellular Sequestration of the Glut4 Glucose Transporter in *Xenopus Oocytes,* J. Biol. Chem. 268:26193–26199, 1993.
Piper et al., GLUT–4 NH$_2$ Terminus Contains a Phenylalanine–Based Targeting Motif that Regulates Intracellular Sequestration, J. Cell Biol. 121:1221–1232, 1993.
Piper et al., The Efficient Intracellular Sequestration of the Insulin–regulatable Glucose Transporter (GLUT–4) is Conferred by the NH$_2$ Terminus, J. Cell Biol. 117:729–743, 1992.
Verhey et al., A Leu–Leu Sequence is Essential for COOH–terminal Targeting Signal of GLUT4 Glucose Transporter in Fibroblasts, J. Biol. Chem. 269:2353–2356, 1994.
Yang et al., Comparison of GLUT4 and GLUT1 Subcellular Trafficking in Basal and Insulin–stimulated 3T3–L1 Cells, J. Biol. Chem. 268:4600–4603, 1993.

*Primary Examiner*—Bradley Sisson
*Assistant Examiner*—Enrique D. Longton
*Attorney, Agent, or Firm*—Fish & Richardson P.C.

[57] ABSTRACT

The invention discloses a chimeric GLUT transporter including a GLUT receptor polypeptide fused to a domain of a detectable heterologous polypeptide and cells expressing such reporter constructs. Cells expressing a detectably-tagged chimeric GLUT transporter are used in methods of screening candidate compounds for their ability to agonize or antagonize an interaction between a ligand and a receptor, e.g., insulin. In addition, a 30 amino acid intracellular retention sequence is disclosed.

7 Claims, 15 Drawing Sheets

SEQ ID NO: 4  ATG GAG CCC AGC AAG AAG CTG ACG GGT CGC CTC ATG CTG GCT GTG GGA GGA GCA GTG CTT GGC
SEQ ID NO: 5  Met Glu Pro Ser Lys Lys Leu Thr Gly Arg Leu Met Leu Ala Val Gly Gly Ala Val Leu Gly>

TCC CTG CAG TTT GGC TAC AAC ACT GGA GTC ATC AAT GCC CCC CAG AAG GTG ATC GAG GAG TTC TAC AAC CAG ACA TGG GTC
Ser Leu Gln Phe Gly Tyr Asn Thr Gly Val Ile Asn Ala Pro Gln Lys Val Ile Glu Glu Phe Tyr Asn Gln Thr Trp Val>

CAC CGC TAT GGA
His Arg Tyr Gly

FIG. 10

```
TTC CGA CGG ACA CCT TCT CTC TTA GAG CAG GAG GTG AAA CCC AGT ACA GAA CTT GAA TAC TTA GGG CCA GAT GAG AAT GAC    SEQ ID NO: 6
Phe Arg Arg Thr Pro Ser Leu Leu Glu Gln Glu Val Lys Pro Ser Thr Glu Leu Glu Tyr Leu Gly Pro Asp Glu Asn Asp   SEQ ID NO: 7
                                                                                                               TCG GCC ACC
                                                                                                               Ser Ala Thr>
```

FIG. 11

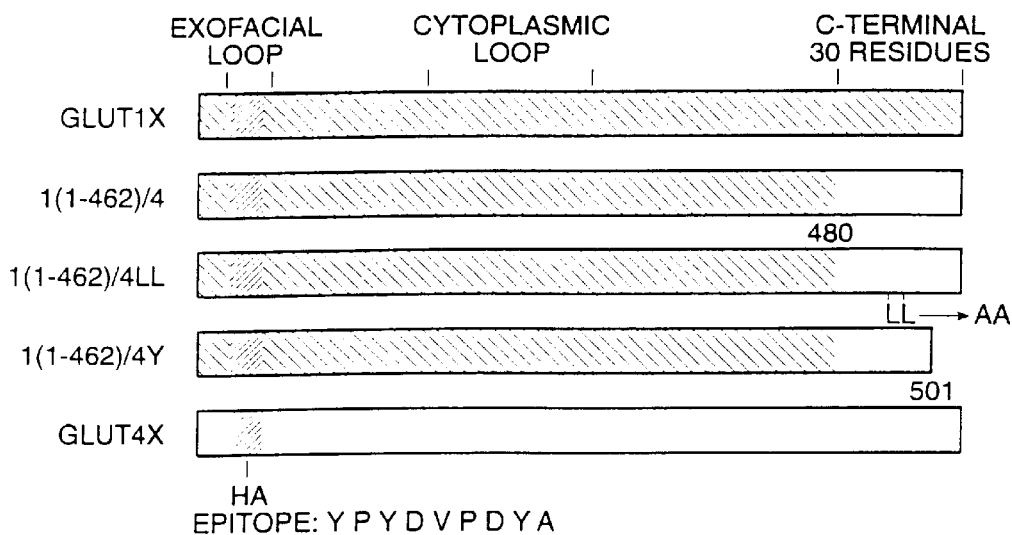
FIG. 12A
FIG. 12B
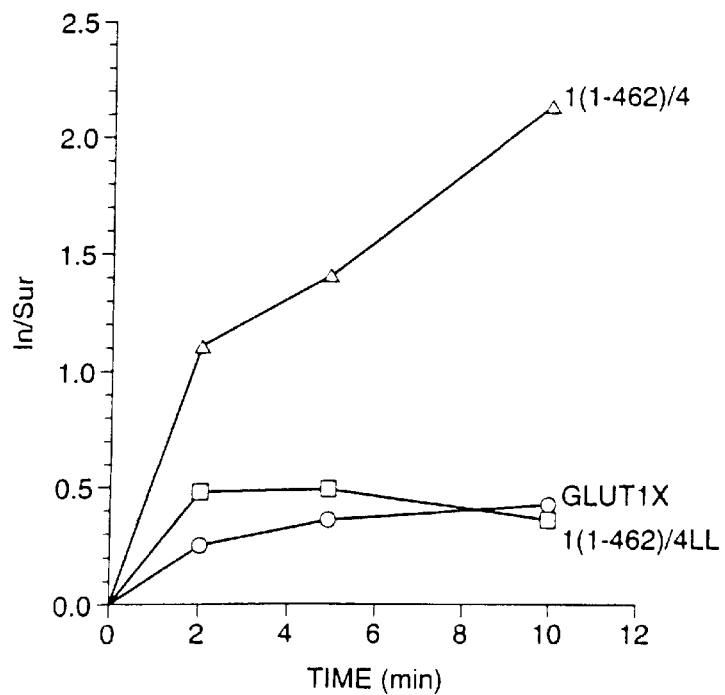
FIG. 17

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 11 amino acids
      (B) TYPE: amino acid
      (D) TOPOLOGY: linear (ii) MOLECULE TYPE: peptide (xi) SEQUENCE DESCRIPTION: SEQ ID NO:1:

Ile Asp Tyr Pro Tyr Asp Val Pro Asp Tyr Ala (2) INFORMATION FOR SEQ ID NO:2:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:2:

```
Ala Tyr Pro Tyr Asp Val Pro Asp Tyr Ala
  1               5                  10
```

(2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:3:

```
Tyr Pro Tyr Asp Val Pro Asp Tyr Ala
  1               5
```

(2) INFORMATION FOR SEQ ID NO:4:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (xi) SEQUENCE DESCRIPTION: SEQ ID NO:4:

```
ATGGAGCCCA GCAGCAAGAA GCTGACGGGT CGCCTCATGC TGGCTGTGGG AGGAGCAGTG     60

CTTGGCTCCC TGCAGTTTGG CTACAACACT GGAGTCATCA ATGCCCCCCA GAAGGTGATC    120

GAGGAGTTCT ACAACCAGAC ATGGGTCCAC CGCTATGGA                            159
```

(2) INFORMATION FOR SEQ ID NO:5:

(i) SEQUENCE CHARACTERISTICS:
        (A) LENGTH: 53 amino acids
        (B) TYPE: amino acid
        (D) TOPOLOGY: linear (ii) MOLECULE TYPE: peptide (xi) SEQUENCE DESCRIPTION: SEQ ID NO:5:

```
Met Glu Pro Ser Ser Lys Lys Leu Thr Gly Arg Leu Met Leu Ala Val
  1               5                  10                  15

Gly Gly Ala Val Leu Gly Ser Leu Gln Phe Gly Tyr Asn Thr Gly Val
                 20                  25                  30

Ile Asn Ala Pro Gln Lys Val Ile Glu Glu Phe Tyr Asn Gln Thr Trp
                 35                  40                  45

Val His Arg Tyr Gly
                 50
```

(2) INFORMATION FOR SEQ ID NO:6:

(i) SEQUENCE CHARACTERISTICS:
        (A) LENGTH: 90 base pairs
        (B) TYPE: nucleic acid
        (C) STRANDEDNESS: single (D) TOPOLOGY: linear (xi) SEQUENCE DESCRIPTION: SEQ ID NO:6:

TCGGCCACCT TCCGACGGAC ACCTTCTCTC TTAGAGCAGG AGGTGAAACC CAGTACAGAA    60

CTTGAATACT TAGGGCCAGA TGAGAATGAC                                    90

(2) INFORMATION FOR SEQ ID NO:7:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:7:

Ser Ala Thr Phe Arg Arg Thr Pro Ser Leu Leu Glu Gln Glu Val Lys
 1               5                  10                  15

Pro Ser Thr Glu Leu Glu Tyr Leu Gly Pro Asp Glu Asn Asp
            20                  25                  30

(2) INFORMATION FOR SEQ ID NO:8:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:8:

Ser Ala Ala Phe His Arg Thr Pro Ser Leu Leu Glu Gln Glu Val Lys
 1               5                  10                  15

Pro Ser Thr Glu Leu Glu Tyr Leu Gly Pro Asp Glu Asn Asp
            20                  25                  30

(2) INFORMATION FOR SEQ ID NO:9:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:9:

Ile Ala Ser Gly Phe Arg Gln Gly Gly Ala Ser Gln Ser Asp Lys Thr
 1               5                  10                  15

Pro Glu Glu Leu Phe His Pro Leu Gly Ala Asp Ser Gln Val
            20                  25                  30

(2) INFORMATION FOR SEQ ID NO:10:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: where Xaa at position 1 is Ser, Ala,
            Ile, or Val
        (A) NAME/KEY: Other
        (B) LOCATION: 2...2
        (D) OTHER INFORMATION: where Xaa at position 2 is Ala, Ser,

```
          Ile, or Val
(A) NAME/KEY: Other
(B) LOCATION: 3...3
(D) OTHER INFORMATION: where Xaa at position 3 is Thr or Ala
(A) NAME/KEY: Other
(B) LOCATION: 4...4
(D) OTHER INFORMATION: where Xaa at position 4 is Phe or Trp
(A) NAME/KEY: Other
(B) LOCATION: 5...5
(D) OTHER INFORMATION: where Xaa at position 5 is Arg, His, or
          Lys
(A) NAME/KEY: Other
(B) LOCATION: 6...6
(D) OTHER INFORMATION: where Xaa at position 6 is Arg, His, or
          Lys
(A) NAME/KEY: Other
(B) LOCATION: 7...7
(D) OTHER INFORMATION: where Xaa at position 7 is Thr or Ile
(A) NAME/KEY: Other
(B) LOCATION: 8...8
(D) OTHER INFORMATION: where Xaa at position 8 is Pro or Hyp
(A) NAME/KEY: Other
(B) LOCATION: 9...9
(D) OTHER INFORMATION: where Xaa at position 9 is Ser or Ala
(A) NAME/KEY: Other
(B) LOCATION: 12...12
(D) OTHER INFORMATION: where Xaa at position 12 is Glu, Asp,
          or Ala
(A) NAME/KEY: Other
(B) LOCATION: 13...13
(D) OTHER INFORMATION: where Xaa at position 13 is Gln or Asn
(A) NAME/KEY: Other
(B) LOCATION: 14...14
(D) OTHER INFORMATION: where Xaa at position 14 is Glu, Asp,
          or Ala
(A) NAME/KEY: Other
(B) LOCATION: 15...15
(D) OTHER INFORMATION: where Xaa at position 15 is Val, Thr,
          or Ser
(A) NAME/KEY: Other
(B) LOCATION: 16...16
(D) OTHER INFORMATION: where Xaa at position 16 is Lys or Arg
(A) NAME/KEY: Other
(B) LOCATION: 17...17
(D) OTHER INFORMATION: where Xaa at position 17 is Pro or Hyp
(A) NAME/KEY: Other
(B) LOCATION: 18...18
(D) OTHER INFORMATION: where Xaa at position 18 is Ser, Thr,
          or Ala
(A) NAME/KEY: Other
(B) LOCATION: 19...19
(D) OTHER INFORMATION: where Xaa at position 19 is Thr, Ser,
          or Ala
(A) NAME/KEY: Other
(B) LOCATION: 20...20
(D) OTHER INFORMATION: where Xaa at position 20 is Glu, Asp,
          or Ala
(A) NAME/KEY: Other
(B) LOCATION: 21...21
(D) OTHER INFORMATION: where Xaa at position 21 is Leu, Ile,
          or Val
(A) NAME/KEY: Other
(B) LOCATION: 22...22
(D) OTHER INFORMATION: where Xaa at position 22 is Glu, Asp,
          or Ala
(A) NAME/KEY: Other
(B) LOCATION: 23...23
(D) OTHER INFORMATION: where Xaa at position 23 is Tyr or Hyp
(A) NAME/KEY: Other
(B) LOCATION: 24...24
(D) OTHER INFORMATION: where Xaa at position 24 is Leu, Ile,
          or Val
(A) NAME/KEY: Other
(B) LOCATION: 25...25
(D) OTHER INFORMATION: where Xaa at position 25 is Gly, Ser,
          or Ala
(A) NAME/KEY: Other
(B) LOCATION: 26...26
(D) OTHER INFORMATION: where Xaa at position 26 is Pro or Hyp
(A) NAME/KEY: Other
```

```
        (B) LOCATION: 27...27
        (D) OTHER INFORMATION: where Xaa at position 27 is Asp, Glu,
            or Ala
        (A) NAME/KEY: Other
        (B) LOCATION: 28...28
        (D) OTHER INFORMATION: where Xaa at position 28 is Glu, Asp,
            or Ala
        (A) NAME/KEY: Other
        (B) LOCATION: 29...29
        (D) OTHER INFORMATION: where Xaa at position 29 is Asn or Gln
        (A) NAME/KEY: Other
        (B) LOCATION: 30...30
        (D) OTHER INFORMATION: where Xaa at position 30 is Asp or
            a salt thereof (xi) SEQUENCE DESCRIPTION: SEQ ID NO:10:

Xaa Xaa Xaa Xaa Xaa Xaa Xaa Xaa Xaa Leu Leu Xaa Xaa Xaa Xaa Xaa
  1               5                  10                  15

Xaa Xaa Xaa Xaa Xaa Xaa Xaa Xaa Xaa Xaa Xaa Xaa Xaa Xaa
             20                  25                  30
```

RECEPTOR-ACTIVATED REPORTER SYSTEMS

This application is a continuation-in-part of application Ser. No. 08/127,316, filed on Sep. 27, 1993 now abandoned.

STATEMENT AS TO FEDERALLY SPONSORED RESEARCH

This invention was made in part with Government funding and the Government therefore has certain rights in the invention.

BACKGROUND OF THE INVENTION

This invention relates to receptor-activated. reporter systems.

Many disease processes adversely affect the normal operation of membrane receptor systems that deliver signals for regulating cellular functions. Effective therapy for such diseases includes drugs that directly interact with the receptor systems in a way that counters the affect of a particular disease process. Even diseases that do not directly affect a receptor signaling mechanism can be fully or partially alleviated by exogenously manipulating signaling by appropriate receptors through drug therapy. Based on these principles, notable successes have been achieved in designing effective drugs to alleviate illnesses, including antidepressants and anti-ulcer drugs.

Many diseases for which no effective therapy exists can also be approached by developing drugs that would interact directly with appropriate receptor systems. These include but are not limited to the insulin receptor signaling systems in muscle, which are defective in Type II diabetes mellitus, the PDGF and IGF-I receptor signaling systems which appear to stimulate abnormal proliferation of smooth muscle cells in coronary artery disease, and lymphokine receptors which mediate inappropriate autoimmune reactions. Development of appropriate drugs that directly effect these and other receptor proteins need to be generated. Efficient development of such drugs require screening of compounds with biological assays that selectively and, perhaps more importantly, efficiently monitor specific receptor activities in response to drug action. In such assays, it is necessary to have a highly sensitive, convenient readout of receptor activity. This disclosure describes discoveries capable of providing such a readout for the activity of the insulin receptor as well as many other receptor systems.

SUMMARY OF THE INVENTION

In general, the invention features a chimeric GLUT transporter including a GLUT transporter polypeptide fused to a detectable heterologous polypeptide. In preferred embodiments, the GLUT transporter is selected from the group including, but not limited to, GLUT1, GLUT2, GLUT3, GLUT4, and GLUT5 and the detectable heterologous polypeptide is fused to an exofacial domain of the GLUT transporter. Such a detectable heterologous polypeptide may include the hemagglutinin (HA) epitope or the c-myc epitope or, alternatively, may include a polypeptide selected from the group including, without limitation, β-galactosidase, β-glucuronidase, alkaline phosphatase, and luciferase. In other preferred embodiments the transporter polypeptide includes an intracellular retention signal and/or an overexpression domain.

In another aspect, the invention features a polypeptide including a GLUT transporter intracellular retention signal. Preferably, such an intracellular retention signal comprises a sequence substantially identical to the amino acid sequence shown in FIG. 11 (SEQ ID NO: 7) or a retention signal fragment thereof.

In another aspect, the invention features a GLUT4 intracellular retention signal. Preferably, such an intracellular retention signal includes a sequence substantially identical to the amino acid sequence shown in FIG. 12 (SEQ ID NO: 7) or in SEQ ID NO: 8 or a GLUT4 intracellular retention signal fragment thereof. In various preferred embodiments, the intracellular retention signal consists of a leucine doublet at positions 10 and 11 of the amino acid sequence shown in FIG. 12 or in SEQ ID NO: 8. In a related aspect, the invention features a substantially isolated polypeptide which is a fragment or analog of a GLUT4 intracellular retention signal including a domain capable of interacting with an insulin mimetic or antagonist.

In another aspect, the invention features an intracellular retention signal polypeptide having the amino acid formula (the sequence beginning with $A^1$ and ending with $A^{28}$ being represented by SEQ ID NO: 10):

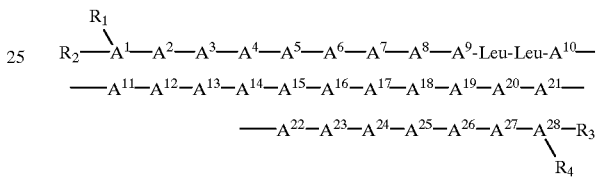

wherein $A^1$ is bonded to each $R_1$ and $R_2$, and $A^{28}$ is bonded to each $R_3$ and $R_4$; wherein each $R_1$, $R_2$, $R_3$, and $R_4$, independently, is H, $C_1$–$C_{12}$ alkyl (e.g., methyl), $C_6$–$C_8$ aryl (e.g., phenyl, napthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$A^1$ is Ser, Ala, Ile, or Val;
$A^2$ is Ala, Ser, Ile, or Val;
$A^3$ is Thr or Ala;
$A^4$ is Phe, or Trp;
$A^5$ is Arg, His or Lys;
$A^6$ is Arg, His or Lys;
$A^7$ is Thr, or Ile;
$A^8$ is Pro or Hyp;
$A^9$ is Ser, or Ala;
$A^{10}$ is Glu, Asp or Ala;
$A^{11}$ is Gln or Asn;
$A^{12}$ is Glu, Asp, or Ala;
$A^{13}$ is Val, Thr, or Ser;
$A^{14}$ is Lys, or Arg;
$A^{15}$ is Pro or Hyp;
$A^{16}$ is Ser, Thr, or Ala;
$A^{17}$ is Thr, Ser, or Ala;
$A^{18}$ is Glu, Asp, or Ala;
$A^{19}$ is Leu, Ile, or Val;
$A^{20}$ is Glu, Asp, or Ala;
$A^{21}$ is Tyr or Hyp;
$A^{22}$ is Leu, Ile, or Val;
$A^{23}$ is Gly, Ser, or Ala;
$A^{24}$ is Pro or Hyp;
$A^{25}$ is Asp, Glu, or Ala;
$A^{26}$ is Glu, Asp, or Ala;

$A^{27}$ is Asn, or Gln;

$A^{28}$ is Asp; or a salt thereof.

Examples of preferred polypeptides have the amino acid formula NH$_2$-Ser-Ala-Thr-Phe-Arg-Arg-Thr-Pro-Ser-Leu-Leu-Glu-Gln-Glu-Val-Lys-Pro-Ser-Thr-Glu-Leu-Glu-Tyr-Leu-Gly-Pro-Asp-Glu-Asn- Asp-COOH (SEQ ID NO: 7) or NH$_2$-Ser-Ala-Ala-Phe-His-Arg-Thr-Pro-Ser-Leu-Leu-Glu-Gln-Glu-Val-Lys-Pro-Ser- Thr-Glu-Leu-Glu-Tyr-Leu-Gly-Pro-Asp-Glu-Asn-Asp-COOH. (SEQ ID NO: 8)

In another aspect, the invention features a polypeptide including a GLUT transporter overexpression domain. Preferably, such an overexpression domain comprises a sequence substantially identical to the amino acid sequence shown in FIG. 10 (SEQ ID NO: 5) or an overexpression domain fragment thereof.

In yet another aspect, the invention features substantially pure DNA which encodes a polypeptide of the invention, e.g, a chimeric GLUT transporter, a retention signal, or an overexpression domain, or any fragments or analogs of the aforementioned polypeptides. The invention also features a vector including the substantially pure DNA and which is capable of directing the expression of the polypeptide encoded by the DNA in a vector-containing cell. Additionally, the invention features a cell which contains the substantially pure DNA, as well as a transgenic animal (e.g., a mammal such as a mouse or a rat) which contains such DNA.

In yet another aspect, the invention features a method of determining whether a candidate compound mimics or antagonizes effects of insulin, the method including: (a) providing a transfected host cell comprising a nucleic acid sequence which encodes a chimeric GLUT transporter comprising a GLUT transporter polypeptide fused to a detectable polypeptide; (b) contacting the transfected host cell with the candidate compound; and (c) measuring the amount of the detectable polypeptide on the surface of the cell in the presence of the candidate compound, an increase or decrease in the polypeptide being indicative that the compound is an insulin mimic or antagonist, respectively.

In another aspect, the invention features a method of determining whether a candidate compound mimics or antagonizes effects of insulin, the method including: (a) providing a transgenic animal comprising a nucleic acid sequence which encodes a chimeric GLUT transporter comprising a GLUT transporter polypeptide fused to a detectable polypeptide; (b) exposing (e.g., by intravenous or intramuscular injection, or by ingestion) the transgenic animal to the candidate compound; and (c) measuring the amount of the detectable polypeptide on the surface of a cell of the animal in the presence of the candidate compound, an increase or decrease in the polypeptide being indicative that the compound is an insulin mimic or antagonist, respectively.

In another aspect, the invention features a method of determining whether a candidate compound mimics or antagonizes effects of a transporter, the method including: (a) providing a transfected host cell comprising a first and second nucleic acid sequence, wherein the first nucleic acid sequence encodes a first chimeric receptor comprising an exofacial receptor capable of binding with the candidate compound fused to an insulin transporter comprising a transmembrane domain and a cytoplasmic domain, and the second nucleic acid sequence encodes a second chimeric GLUT transporter comprising a GLUT transporter polypeptide fused to a detectable polypeptide; (b) contacting the transfected host cell with the candidate compound; and (c) measuring the amount of the detectable polypeptide on the surface of the cell in the presence of the candidate compound, an increase or decrease in the polypeptide being indicative that the compound is a mimic or antagonist of the first chimeric receptor, respectively. Preferably, the exofacial domain of the first chimeric transporter is selected from the group consisting of the EGF receptor tyrosine kinase, the PDGF receptor tyrosine kinase, the FGF receptor tyrosine kinase, the CSF receptor tyrosine kinase, IL-2, IL-4, IL-6, activin receptor and transforming growth factor receptor, and growth hormone receptor.

In another aspect, the invention features a method of determining whether a candidate compound mimics or antagonizes effects of a transporter, the method including: (a) providing a transgenic animal comprising a first and second nucleic acid sequence, wherein the first nucleic acid sequence encodes a first chimeric receptor comprising an exofacial transporter domain capable of interacting with the candidate compound fused to an insulin receptor comprising a transmembrane domain and a cytoplasmic domain, and the second nucleic acid sequence encodes a second chimeric GLUT transporter comprising a GLUT transporter polypeptide fused to a detectable polypeptide; (b) exposing (e.g., by intramuscular or intravenous injection, or by ingestion) the transgenic animal with the candidate compound; and (c) measuring the amount of the detectable polypeptide on the surface of a cell of the animal in the presence of the candidate compound, an increase or decrease in the surface polypeptide being indicative that the compound is a mimic or antagonist of the first chimeric receptor, respectively.

In a final aspect, the invention features a method of determining whether a candidate compound mimics or antagonizes effects of insulin, the method including: (a) providing the intracellular retention signal of the intracellular retention signal fused to a support; (b) contacting the retention signal with the candidate compound; and (c) measuring the amount of the candidate retention domain, an increase or decrease in the binding of the compound being indicative of that the compound as an insulin mimic or antagonist, respectively. Preferably, the intracellular retention signal is the GLUT4 intracellular retention signal (SEQ ID NO: 7 or SEQ ID NO: 8).

By "exofacial" is meant positioned extracellularly.

By "substantially pure" is meant that the chimeric GLUT transporter polypeptide provided by the invention is at least 60%, by weight, free from the proteins and naturally-occurring organic molecules with which it is naturally associated. Preferably, the preparation is at least 75%, more preferably at least 90%, and most preferably at least 99%, by weight, chimeric GLUT transporter polypeptide. A substantially pure GLUT transporter polypeptide may be obtained, for example, by extraction from a natural source (e.g., a mammalian liver cell); by expression of a recombinant nucleic acid encoding a GLUT transporter polypeptide, or by chemically synthesizing the protein. Purity can be measured by any appropriate method, e.g., column chromatography, polyacrylamide gel electrophoresis, or HPLC analysis.

By a "polypeptide" is meant any chain of amino acids, regardless of length or post-translational modification (e.g., glycosylation)

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein or domain (assayed, e.g., as described herein).

A "substantially identical" nucleic acid sequence codes for a substantially identical amino acid sequence as defined above.

By a "detectable heterologous polypeptide" is meant any chain of amino acids regardless of length or post-translational modification which is capable of being assayed, e.g, by immunologic or colorimetric detection. By "heterologous" is meant derived from a source other than the GLUT transporter to which the polypeptide is found.

By "overexpression" is meant a chain of amino acids which is capable of inducing the expression of a GLUT transporter polypeptide in whose sequence it is included.

By "intracellular retention signal" is meant a chain of amino acids which is capable of signalling a GLUT transporter polypeptide in whose sequence it is included to remain within a compartment found within a cell, e.g., the Golgi apparatus.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

The symbols $A^x$ (e.g., $A^1$) and the like; and Ser, Leu and the like, as found in a peptide sequence infra, stands for amino acid residues, e.g., =N—CH(R)—CO— when it is at the N-terminus, —CH(R)—COOH when it is at the C-terminus, or —NH—CH(R)— when it is at any other position. For example, R is —CH$_2$COOH for Asp, R is —H for glycine and R is —CH$_2$OH for Ser. When an amino acid residue is optically active, it is the L-form configuration that is intended unless the D-form is expressly designated. All amino sequences mentioned herein are written according to usual convention whereby the N-terminal amino acid is on the left and the C-terminal amino acid sequence is on the right. A short line between two amino acid residues indicates a peptide bond. The conventional abbreviations for the various amino acids are used.

The invention provides new methodologies which afford direct, unambiguous assessment of glucose transporter proteins at the cell surface membrane in response to insulin receptor activity. Such a technique could be used in any number of ways; for example, to monitor a compound that mimics or antagonizes the insulin receptor.

Other features and advantages of the invention will be apparent from the following description of the preferred embodiments thereof, and from the claims.

DESCRIPTION

The drawings will first be briefly described.
Drawings

FIG. 1 is a schematic representation of two GLUT transporter constructs which: (1) display a characteristic GLUT4 intracellular localization and response to insulin; (2) are readily expressed at high levels in cultured cells; and (3) are readily detected at cell surface using an exofacial epitope tag or enzyme activity.

FIG. 2 is a schematic representation of an insulin-responsive GLUT chimera reporter constructs using the unique C-terminus region of GLUT4 (SEQ ID NO:7; SEQ ID NO:8). When expressed in insulin responsive cells, these constructs provide large 20–40-fold increases in signal in response to insulin.

FIG. 3 is a schematic representation of a dual chimera reporter system for development of drugs directed against the exofacial ligand binding domains of a plurality receptor proteins.

FIG. 4 is a panel of schematic diagrams depicting several HA epitope-tagged chimeras and their comparison with GLUT1 and GLUT4 sequences. The location of the HA-tag is indicated by the hatched areas at the NH$_2$ terminus or in the exofacial loop. GLUT1N has the HA sequence YPYD-VPDYA (SEQ ID NO: 3) inserted immediately after the methionine start codon. GLUT4N has the sequence AYPY-DVPDYA (SEQ ID NO:2) following the first methionine. HA tags in the exofacial loop of chimeras containing GLUT1 sequences in the NH$_2$ terminus have the tag IDY-PYDVPDYA (SEQ ID NO:1) inserted after amino acid 53. Exofacial HA tags in chimeras containing GLUT4 NH$_2$ termini have the epitope IDYPYDVPDYA (SEQ ID NO:1) inserted after amino acid 83. The amino acids I and D are added to insert a unique ClaI restriction site to confirm orientation. Chimera IM4 contains amino acid 1–199 of GLUT1, the amino acids 215–295 from GLUT4 corresponding to the middle loop, and GLUT1 amino acids 280–492. GLUT1/4LL contains the amino acid sequence of GLUT1 except that GLUT1 amino acids 319–327 have been replaced with amino acids 335–343 from GLUT4. Chimera 1(1–462)/4 replaces the last 29 amino acids of GLUT1 with the corresponding 30 amino acids of GLUT4. Chimera 1(1–199)/4 contains amino acids 1–199 of GLUT1 and amino acids 216–509 of GLUT4 which correspond to the rest of the molecule. Chimera 1(1–53)/4 contains the first 53 amino acids of GLUT1, the HA epitope and amino acids 66–509 of GLUT4.

FIG. 5 is a panel of immunofluorescent photomicrographs showing HA-tagged GLUT1 and GLUT4 transporters transiently expressed in COS-7 cells. COS-7 cells transiently transfected with the indicated constructs were fixed in 4% formaldehyde 48 hours after transfection. Cell surface transporters (SURFACE) were detected by incubation with anti-HA antibody (12CA5), and FITC-conjugated goat anti-mouse IgG before permeabilization. The cells were then permeabilized and total cellular transporters (TOTAL) were detected with anti-HA antibody and rhodamine-coupled goat anti-mouse (GLUT1) or anti-GLUT4 antibody (R1288) and rhodamine-coupled goat anti-rabbit antibodies (GLUT4). Bar, 10 μm.

FIG. 6 is a panel of immunofluorescent photomicrographs of HA-tagged GLUT1X, GLUT4X, and three transporter chimeras (1(1-199), 1(1-462)/4, and 4(1-478)/1) transiently expressed in COS-7 cells transiently transfected with the indicated constructs were fixed in 4% formaldehyde 48 h after transfection. Cell surface (SURFACE) and total (TOTAL) immunoreactivity was analyzed as described in the legend to FIG. 5, Bar, 10 μm.

FIG. 7 is a panel of immunofluorescent photomicrographs showing the effect of expression level on cell surface localization of GLUT1X, GLUT4X, and three transporter chimeras (1(1-462)/4, 1(1-199)4, and 1(1-53)/4) transiently expressed in COS-7 cells. COS-7 cells transiently transfected with the indicated constructs were fixed in 4% formaldehyde 48 hours after transfection. Cell surface (SURFACE) and total (TOTAL) immunoreactivity was analyzed as described in FIG. 5 (supra). Two different levels of expression of each construct were analyzed. Top panels of both galleries represent cells with low expression levels, whereas bottom panels in both galleries represent cells with higher expression levels. Bar, 10 μm.

FIG. 8 is a panel of immunofluorescent photomicrographs of transporter chimeras 1/M4 and 1/4LL transiently expressed in COS-7 cells. COS-7 cells transiently transfected with the indicated constructs were fixed in 4% formaldehyde 48 hours after transfection, and analyzed as described in FIG. 5.

FIG. 9 is a panel of photomicrographs showing the immunofluorescence localization of GLUT1, GLUT4, and two transporter chimeras stably expressed in CHO cells. CHO-K1 cells stably expressing GLUT4N, GLUT1X, HA-tagged 1(1- 199)/4, and two lines of untagged 1(1-462)/4 expressing the construct at low and high levels were grown on coverslips. The cells were fixed, permeabilized with PBS+1% FBS+0.5% Triton X-100, and expression detected with antibodies against HA (GLUT1, GLUT4, 1(1-199)/4 or against a COOH-terminal terminal GLUT4 polypeptide (1(1-462)/4). Primary antibodies were detected with FITC conjugated anti-mouse or anti-rabbit antibodies, Images represented total staining within the cell. 1(1-462)/4 clone A is a low expressing cell line. 1(1-462)/4 clone B is a high expressing cell line. Arrowheads mark intracellular staining in 1(1-462)/4 clone B. Bar, 10 µm.

FIG. 10 shows the nucleotide sequence (SEQ ID NO: 4) and deduced amino acid sequence of the overexpression domain (SEQ ID NO: 5).

FIG. 11 shows the nucleotide sequence (SEQ ID NO: 6) and deduced amino acid sequence of the intracellular retention signal (SEQ ID NO: 7).

Figure 1:
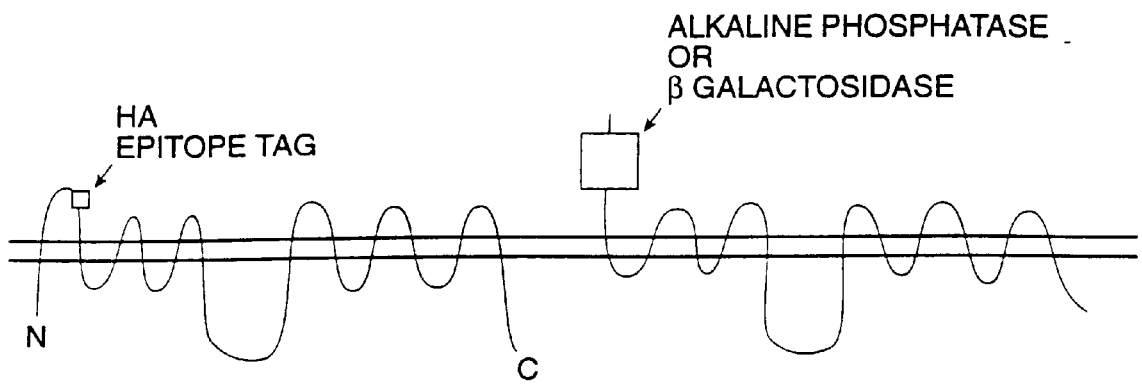

FIG. 12 is a panel of schematic diagrams depicting several HA epitope-tagged chimeras and mutant chimeras and their comparison to the full length GLUT1 and GLUT4 transporters (Panel A), and the amino acid sequence of rGLUT4C (amino acids 480–509) and hGLUT1C (amino acids 480–509). The location of the HA epitope tag insert (IDYPYDVPDYA) in the exofacial loop is indicated by the hatched area. This epitope is inserted after amino acid 53 in all transporters except GLUT4X in which the HA sequence is inserted after amino acid 83. GLUT1X and GLUT4X contain the entire sequence of the appropriate isoform. The construct 1(1-462)/4 contains the first 462 amino acids of GLUT1 and the last 30 amino acids of GLUT4. For 1(1-462)/4LL the leucines indicated by asterisks in panel B been mutated to alanine residues. Construct 1(1-462)/4Y is truncated at amino acid number 503 so that the tyrosine at position 504 and the rest of the molecule is missing.

Figure 13:
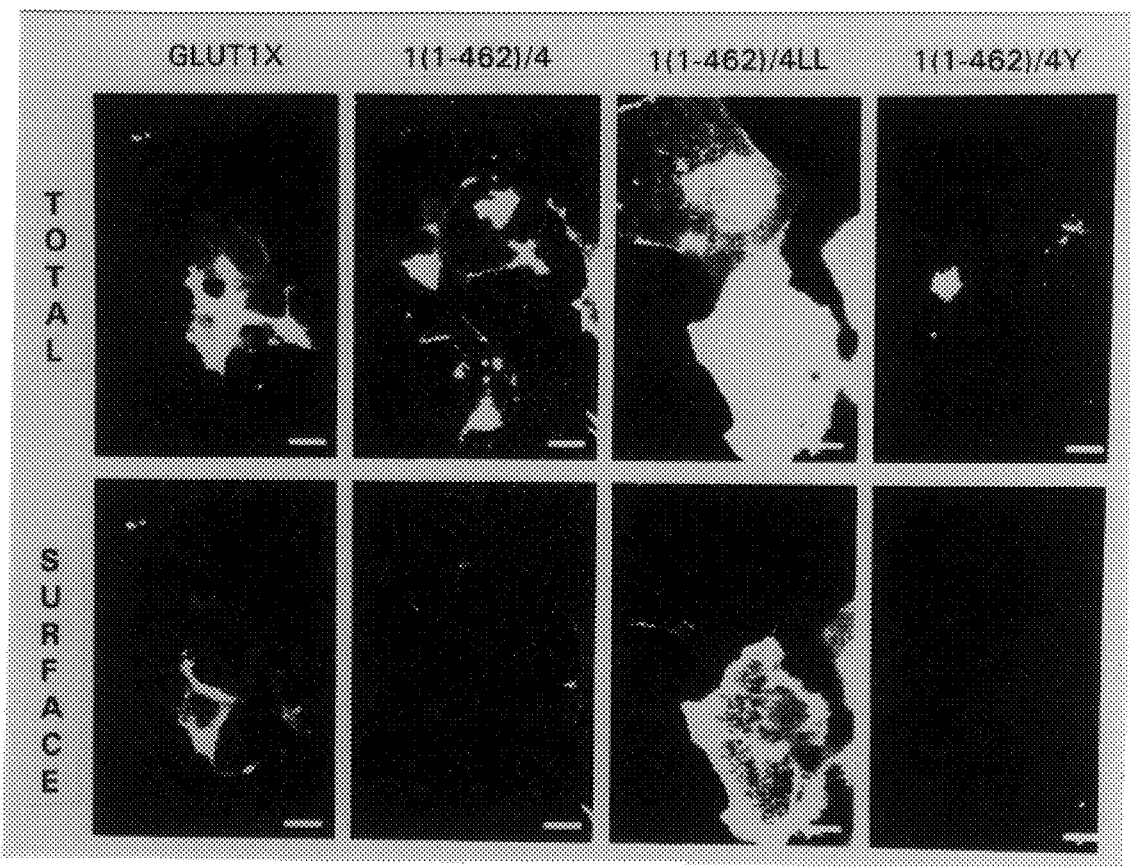

FIG. 13 is a panel of immunofluorescent photomicrographs of HA-tagged transporter constructs transiently expressed in COS-7 cells. COS-7 cells were fixed in 4% formaldehyde 48 hours after transfection with the indicated constructs. Transporters present at the cell surface (SURFACE) were detected with anti-HA antibody (12CA5) and FITC-conjugated anti-mouse second antibody prior to permeabilizing the cells. The cells were permeabilized and total transporter expression (TOTAL) was detected with anti-HA (for GLUT1X) or anti-GLUT4 (R1288) (for chimeras) antibody and rhodamine-coupled anti-mouse (for anti-HA) or anti-rabbit (for anti-GLUT4) second antibody. To accurately quantify the proportion of each transporter present at the cell surface of translocated cells, the fluorescence intensity (Rhodamine and FITC) of all transfected cells found in 10 fields (10–15 cells) for each construct was measured. The ratios of surface/total fluorescence obtained were expressed as mean±SEM, and were 0.51±0.08, 0.18±0.05 and 0.51±0.10 for GLUT 1X, 1(1-462)/4 and 1(1-462)/4LL respectively. Bar, 10 µm.

Figure 14:
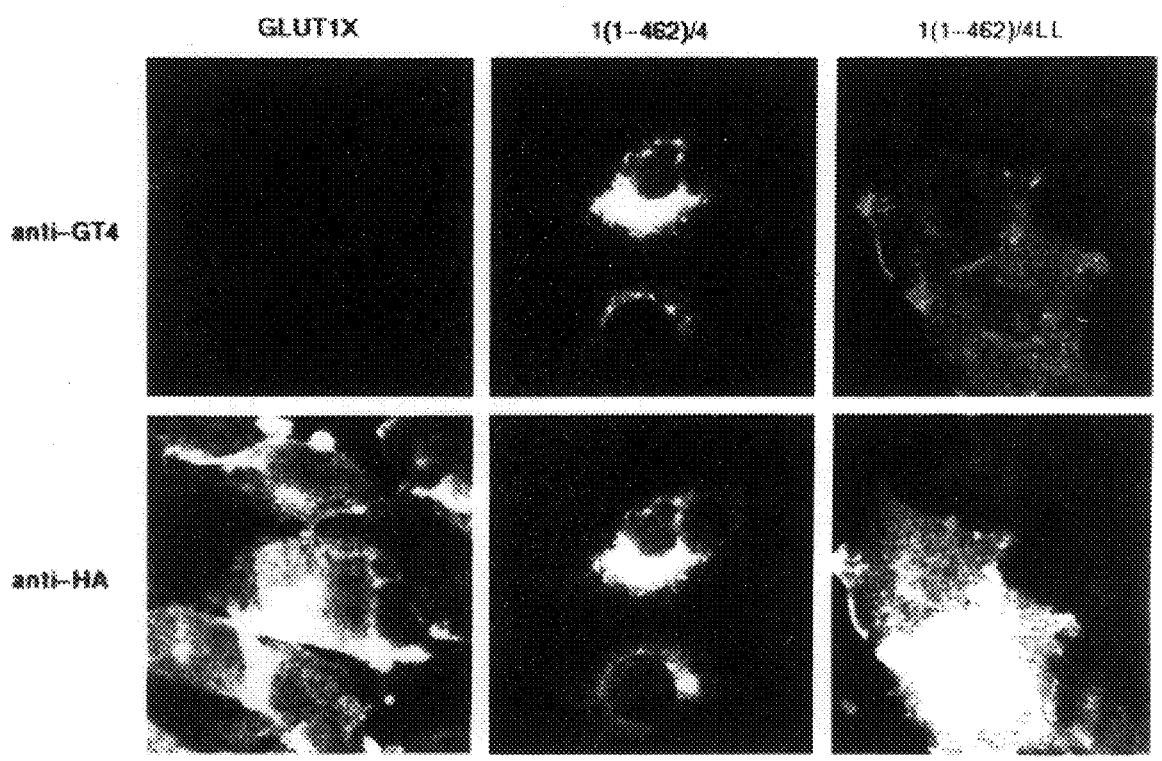

FIG. 14 is a panel of immunofluorescent photomicrographs of CHO cells expressing GLUT1X, 1(1-462)/4, and 1(1-462)/4LL. CHO cells expressing the indicated chimeras were fixed in 4% formaldehyde and permeabilized. Immunoreactivity with anti-HA (lower panels) and anti-GLUT4 (R1288) antibodies (upper panels) was detected with FITC-coupled anti-mouse and rhodamine-coupled anti-rabbit antibodies, respectively. Bar, 10 µm.

Figure 15:
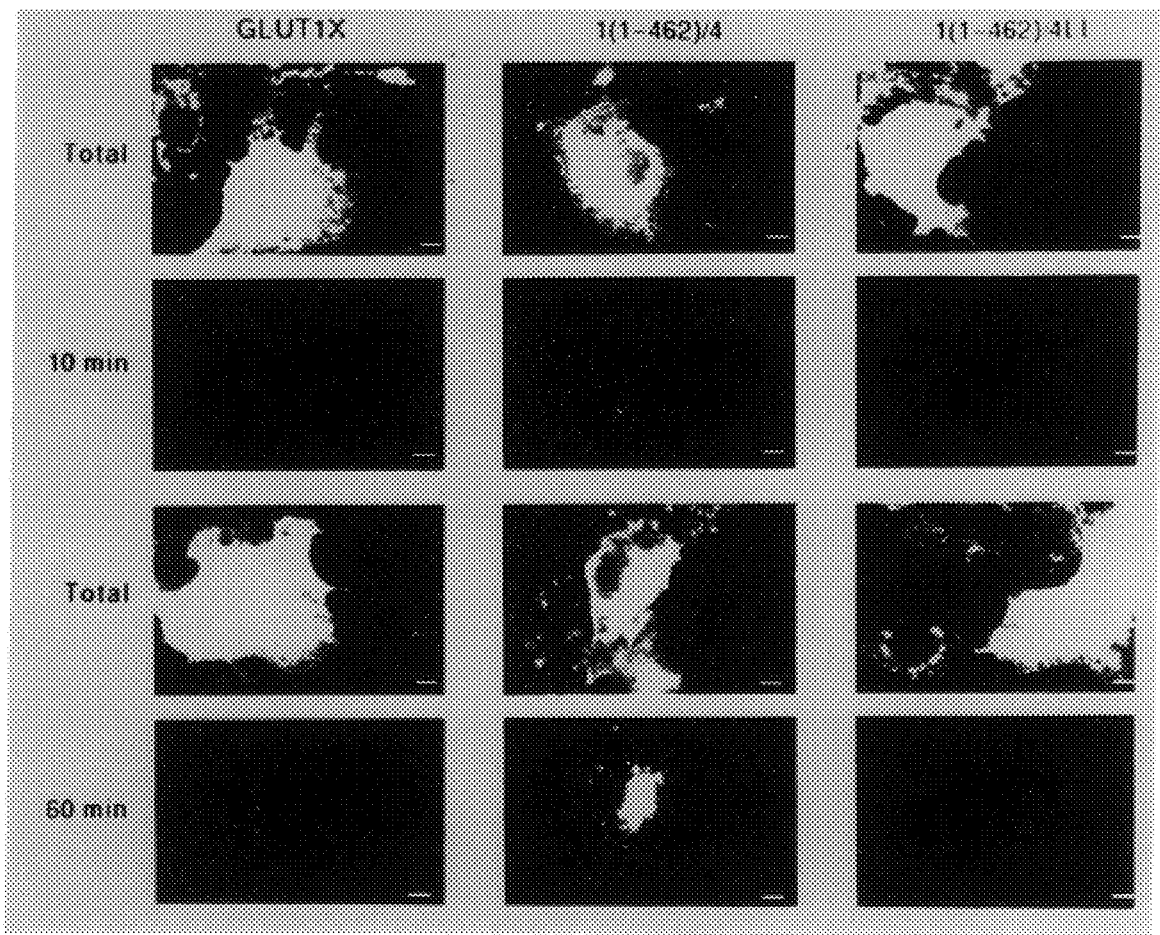

FIG. 15 is a panel of immunofluorescent photomicrographs depicting anti-HA antibody internalization in COS-7 cells transiently expressing HA-tagged transporter chimeras. 48 hours after transfection with the indicated constructs, cells were incubated at 37° C. with anti-HA IgG for 10 min (upper panels) or 60 min (lower panels). Cells were washed on ice, fixed in 4% formaldehyde, and permeabilized. Internalized antibody was detected with FITC-conjugated anti-mouse antibody. Total transporter expression (TOTAL) was analyzed as indicated in the legend of FIG. 13. Bar, 10 µm.

Figure 16:
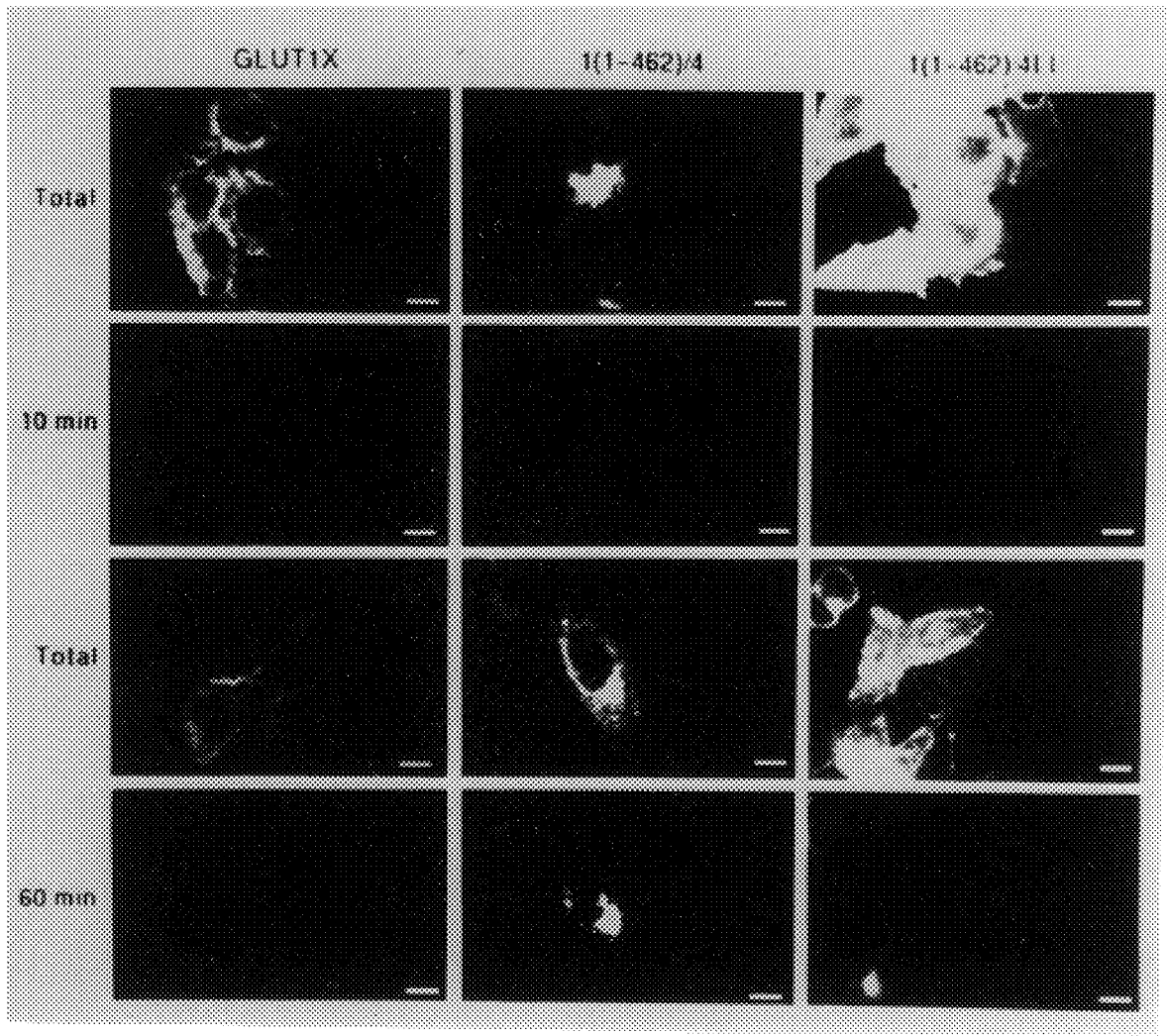

FIG. 16 is a panel of immunofluorescent photomicrographs depicting anti-HA antibody internalization in CHO cells expressing HA-tagged transporter chimeras. CHO cells expressing the indicated transporters were incubated at 37° C. with anti-HA IgG for 10 min (upper panels) or 60 min (lower panels). Cells were washed on ice, fixed in 4% formaldehyde, and permeabilized. Internalized antibody was detected with FITC-conjugated anti-mouse antibody. Total transporter expression (TOTAL) was analyzed as indicated in the legend of FIG. 13. Bar, 10 µm.

FIG. 17 is a graph illustrating initial rate determinations of antibody internalization from CHO cells expressing GLUT1X, 1(1-462)/4, and 1(1-462)/4LL. CHO cells expressing the indicated constructs were incubated at 4° C. for 60 minutes with $^{125}$I HA IgG and washed on ice. The cells were then incubated at 37° C. for 2, 5, or 10 minutes. After washing, the surface bound antibody was released using acidic buffer and counted. The cells were solubilized and internalized counts were determined. The cpm were corrected for cell number. The ratio of internalized counts to surface counts (IN/SUR) was determined and plotted vs. time for each cell line.

Figure 18:
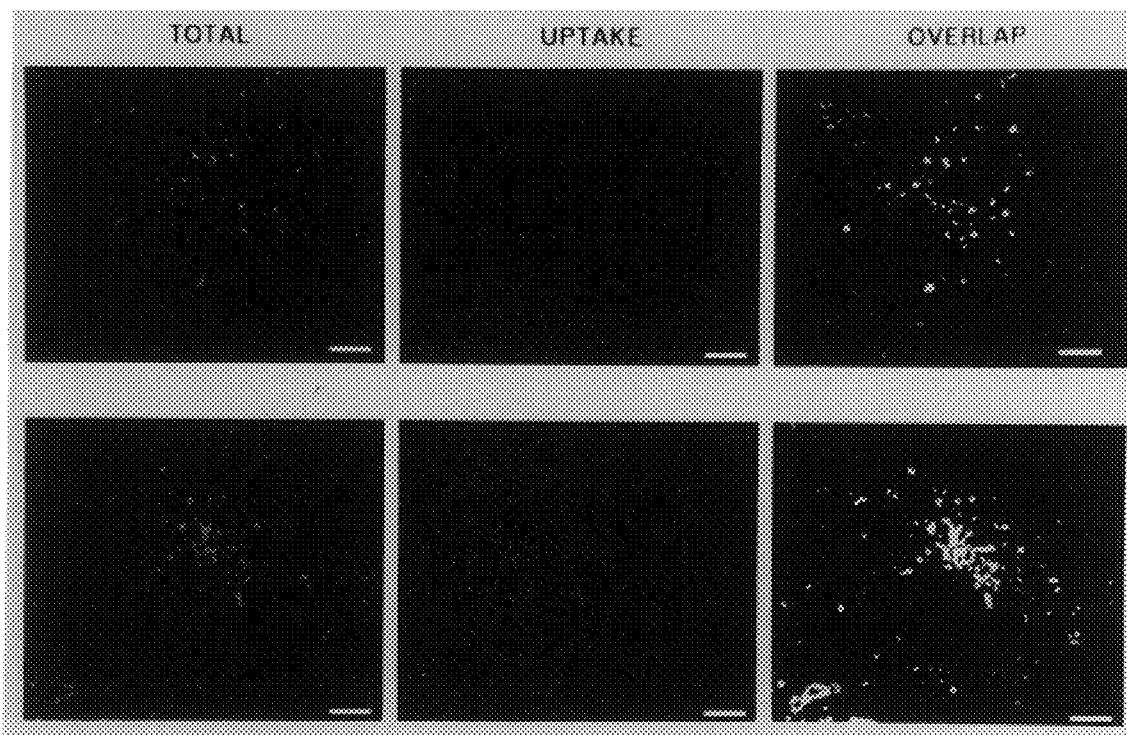

FIG. 18 is a panel of immunofluorescent photomicrographs depicting the co-localization of internalized antibody and expressed transporter 1(1-462)/4 in transiently transfected COS-7 cells. 48 hours after transfection, cells were incubated in anti-HA IgG for 60 minutes at 37° C. The cells were washed on ice and fixed in 4% formaldehyde. Permeabilized cells were then incubated with FITC-conjugated anti-mouse antibody (green, UPTAKE). Total transporter expression (red, TOTAL) was analyzed as indicated in the legend of FIG. 13. Thirty two-dimensional images were taken at 0.25 µm intervals. The background was subtracted and blurring above and below the plane of focus was reversed. Images shown are single optical sections from the middle of the cell. Obvious areas of correspondence were observed in all optical planes, and the coordinates of these areas were used to overlap the images. Co-localization of signal is represented by the white areas in the OVERLAP panels. Bar, 10 µm.

Figure 19:
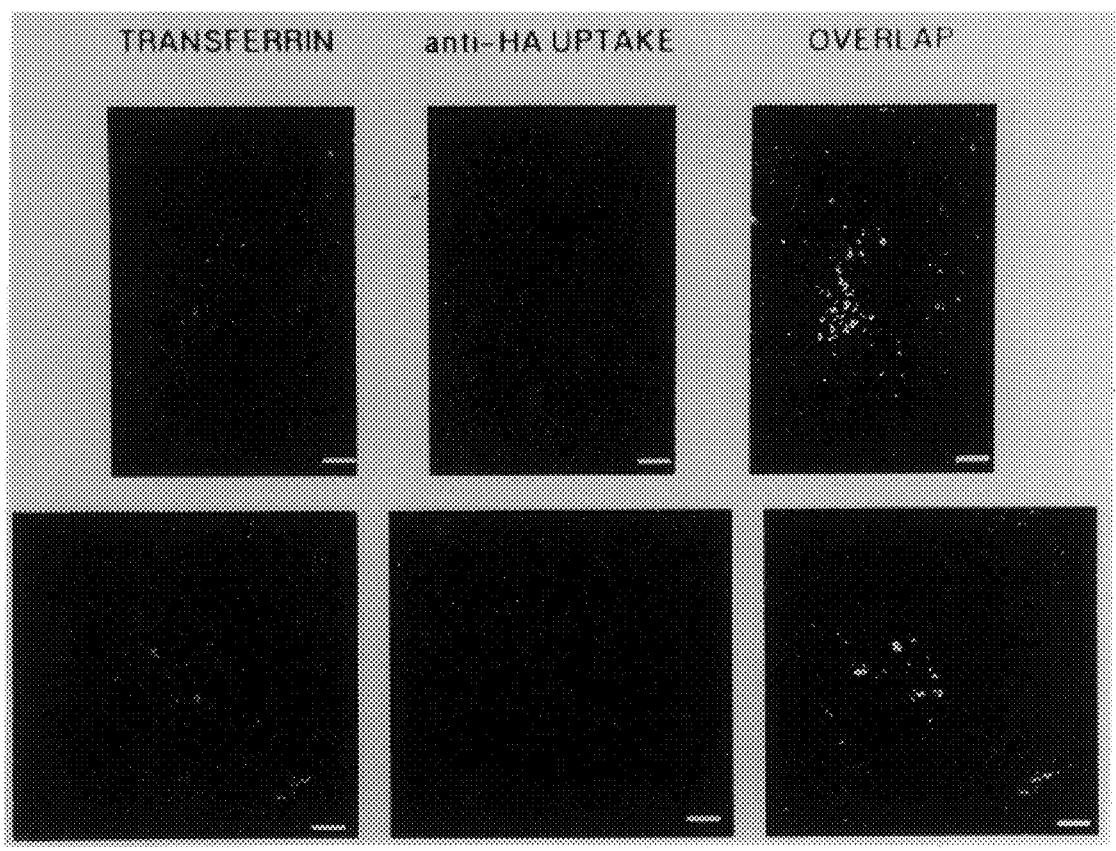

FIG. 19 is a panel of immunofluorescent photomicrographs depicting the co-localization of internalized anti-HA antibody and transferrin in COS-7 cells transiently expressing 1(1-462)/4. 48 hours following transfection, cells were incubated with Texas red labeled transferrin (red, TRANSFERRIN) and anti-HA IgG for 60 minutes. After washing, fixation, and permeabilization, internalized antibody was detected with FITC-conjugated anti-mouse antibody (green, UPTAKE). Images were analyzed as described in FIG. 18. Co-localization of signal is represented by the white areas in the OVERLAP panels. Bar, 10 µm

GLUCOSE TRANSPORTER PROTEINS (GLUT TRANSPORTERS)

Glucose is a basic source of energy for mammalian cells whose metabolism provides ATP under both aerobic and anaerobic conditions. The transport of glucose across the plasma membrane is carried out by two gene families. This invention is concerned with the facilitative glucose transporter (GLUT) family of glucose carriers that are present on the surface of all cells.

Insulin stimulation of adipose and muscle cells results in rapid and marked translocation of GLUT transporter proteins, e.g., the GLUT4 glucose transporter, to the cell surface. Prior to the compounds and methods of the invention, there had not been an efficient method for detecting GLUT-4 translocation because attempts to generate antibodies to the extracellular domain of GLUT-4 have been unsuccessful.

This invention, in general terms, consists of transfecting insulin-sensitive cells with a GLUT4 construct which contains an epitope tag in the extracellular domain. In addition to allowing measurement of the effect of insulin on GLUT-4 translocation, this invention can be used to screen for drugs which mimic the activity of insulin. Furthermore, the invention can be used to screen for molecules which interact with other receptors. This can be achieved by co-expressing epitope tagged GLUT-4 with a chimeric receptor containing the extracellular domain of a given receptor fused to the transmembrane and intracellular domains of the insulin receptor. An additional component of the invention involves the identification of 30 amino acid sequence at the carboxy terminus of GLUT4 which functions as an intracellular retention signal in unstimulated cells. This retention signal functions on heterologous proteins, and thus, can be part of a reporter system for monitoring insulin receptor activity when coupled to an extracellular reporter protein. The following sections describe the aforementioned features of the invention.

Chimeric GLUT Transport Proteins

The invention, in general terms, involves the use of novel glucose transporter proteins that are encoded by cDNA constructs engineered to include a detectable protein (e.g. an antibody epitope such as the HA agglutinin or the c-myc epitope, or a protein domain useful in a colorimetric or flurometric assay such as β-galactosidase or luciferase, respectively) in an exofacial amino acid loop (see e.g., FIG. 1). Additionally, the functional domains of the GLUT transporter protein may be swapped with the domains of other members of the GLUT transporter family (see, e.g., Bell et al., 1993) in order to produce detectable chimeric GLUT transporters having novel properties as described below. Construction of such chimeric GLUT transporter fusion genes is carried out by standard techniques of molecular biology. Additionally, construction of suitable vectors containing the desired coding and control sequences employs standard techniques that are well understood in the art. Thus, isolated plasmids, DNA sequences, or synthesized oligonucleotides are cleaved, tailored, and religated in the form desired. DNA sequences encoding GLUT transporter polypeptides are well known in the art (see, e.g., Mueckler et al., 1985. *Science* 229:941–945; Birnbaum et al., 1986. *Proc. Natl. Acad. Sci.* 83:5784–5799; Asano et al. 1988. *Biochem. Biophys. Res. Commun.* 154:1204–1211; Thorens et al. 1988. *Cell* 55:281–290; Kayano et al., 1988. *J. Biol. Chem.* 263:15245–15248; James et al., 1989. *Nature* 338:83–87; Charron et al., 1989. *Proc. Natl. Acad. Sci.* 86:2535–2539; Kaestner et al., 1989. *Proc. Natl. Acad. Sci.* 86:3150–3154; Fukumoto et al., 1989. *J. Biol. Chem.* 264:7776–7779; Permutt et al., 1989. *Proc. Natl. Acad. Sci.* 86:8688–8692; Gould et al., 1990. *Trends Biochem. Sci.* 15:18–23, all hereby incorporated by reference).

Detectable Reporter Genes

Any suitable detectable reporter gene whose expression may be assayed can, if desired, be used for constructing a chimeric GLUT transporter polypeptides. Such genes include, without limitation, antibody epitopes, e.g., HA hemagglutinin and c-myc epitope (see, e.g., Kansai et al., 1993. *J. Biol Chem.* 268:14523–14526) whose domains provide readily detectable immunological markers and protein domains, e.g., β-galactosidase, β-glucuronidase, alkaline phosphatase, and luciferase, whose enzymatic activity provides a facile assay for detection of a chimeric GLUT transporter protein. Methods for assaying such reporters are performed according to standard methods well known in the art. Thus, any number of antibodies could be made of very high affinity against any number of potential epitopes and DNA encoding such epitope incorporated into the chimeric construct as discussed infra. Similarly, the tagging method is not limited to tags such as antibody epitopes, but also includes protein domains that have functions that can be assayed (e.g., those described supra).

Next, the engineered chimeric GLUT transporter fusion gene is expressed in an appropriate host cell or organism. Methods for transfecting a variety of host cells (e.g., prokaryotic, yeast, insect and mammalian cells), and for creating transgenic animals (see e.g., Leder et al. U.S. Pat. No. 4,736,866 and Leder et al. U.S. Pat. No. 5,175,383) are according to standard techniques well known in the art. Accordingly, the newly inserted sequences serve as detectable markers on the surface of cells that display the glucose transporter proteins in response to insulin receptor action.

Chimeric GLUT transporters can be modified in any number of ways by incorporating additional features of the invention as described below.

Overexpression Sequences

We have discovered that DNA sequences encoding the N-terminal 53 amino acids of the GLUT1 glucose transporter protein confer high levels of expression of the GLUT transporter protein. Thus, the GLUT1(1-53) (SEQ. ID NO: 5) sequence may be included in any chimeric GLUT transporter fusion gene (see e.g., FIG. 10). For example, by substituting the N-terminal 53 amino acids from the GLUT1 glucose transporter protein onto the GLUT4 transporter protein cDNA sequence, much higher expression levels of the transporter protein was observed in COS cells. This discovery leads to a significant improvement over the use of the detectably-tagged GLUT4 transporter protein, in that it allows the production of cell lines expressing large amounts of this detectably-tagged GLUT1/GLUT4 chimera. The chimera protein not only expresses in cells at high levels, but also displays an intracellular localization characteristic of the native GLUT4 protein. Thus, this exofacial GLUT1/GLUT4 chimera tagged with the HA agglutinin (designated below as 1(1-53)/4) represents a glucose transporter protein that can be readily transfected into a variety of cell types with resultant high expression level of protein and easily assessed for its presence on the cell membrane by HA antibody, and behaves like the normal insulin-responsive glucose transporter protein, GLUT4 in its overall membrane trafficking. Accordingly, fragments or analogs of the overexpression domain may be prepared and tested using the assays described herein, as well as according to methods well known in the art.

Intracellular Retention Sequences

Figure 2:
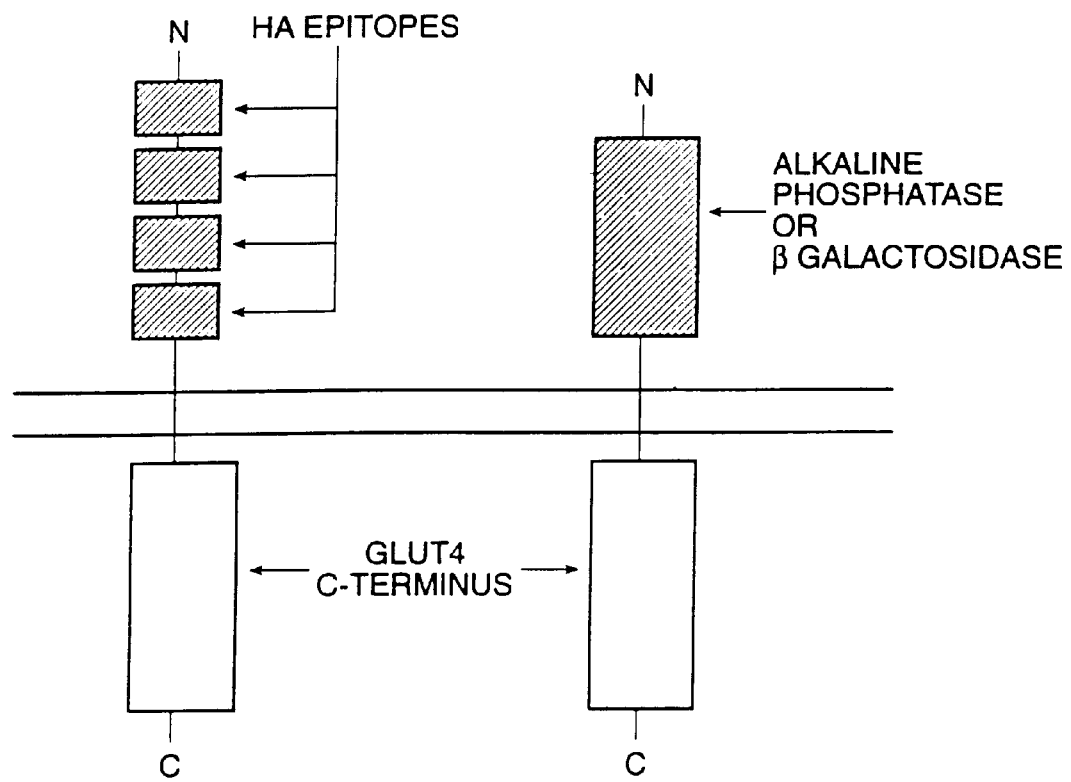

Additionally, it has been discovered that the carboxyterminal 30 amino acids of GLUT4 regulate intracellular localization (see e.g., FIG. 2 and FIG. 11). Thus, by substituting these 30 amino acids onto the a GLUT transporter protein which normally distributes to the cell surface, e.g., GLUT1, causes the retention of a chimera in the intracellular compartment. The structure assumed by this 30 amino acid sequence at the carboxyterminus of GLUT4 appears to be a retention signal by virtue of its ability to interact with cellular molecules that direct it to an intracellular location, e.g., in the Golgi apparatus. Insulin action apparently releases this retention process, allowing these transporter proteins to move to the cell surface membrane.

The fact that this retention signal acts not only on GLUT4, but can also confer to the GLUT1 protein an intracellular localization, reveals the use of this 30 amino acid structure in the construction of other reporters for insulin action. For example, cDNA constructs engineered to contain a reporter epitope on an exofacial portion (HA epitope, or other reporter protein component), a transmembrane domain, and an intracellular portion containing the 30 amino acid retention signal could be used for rapid and efficient reporting of the insulin receptor signal in 3T3-L1 adipocytes, L6 myotubes in culture, or in fat or muscle cells from transgenic animals containing this construct. Thus, this 30 amino acid retention signal can serve, if desired, as part of an efficient biological reporter system (intracellular domain moving to cell surface domain) when coupled to an extracellular reporter polypeptide or protein in response to insulin receptor activity (see FIG. 5 for possible reporter constructs). Accordingly, fragments or analogs of the intracellular retention signal may be prepared and tested using the assays described herein, as well as according to methods well known in the art.

Chimeric Glut Transporter Proteins As Reporters of Receptor Activity

Expressing a chimeric GLUT transporter in cultured cells highly responsive to insulin (e.g., 3T3-L1 adipocytes or L6 myotubes) provides a highly sensitive assay for insulin action (e.g., by using an anti-HA antibody to detect cell surface chimeric GLUT transporter proteins tagged with the HA hemagglutinin epitope) in response to insulin. Ordinarily, this method involves reacting intact cells (unstimulated or stimulated with insulin) with anti-HA antibody, then measuring the amount of antibody bound by second antibody that is labeled or conjugated to a reporter molecule.

Additionally, expression of the exofacial-tagged 1(1-53)/4 transporter protein in intact animals using transgenic technology would allow isolated fat cells or muscle to be rapidly screened for drugs that mimic or inhibit insulin action on glucose transporters using anti-HA antibody. Different antibodies could be made of very high affinity against other potential epitopes to be used in this system. Accordingly, the exofacial-tagging method is not restricted to antibody epitopes, but could include other protein domains that act as readouts (e.g., galactosidase, alkaline phosphatase, etc.) by virtue of their enzymatic activity. In this case, the exofacial loop of the GLUT4 cDNA would be fused with that encoding the reporter protein. Thus, a color reaction could be used as an assay reporting the cell surface localization of this region of the transporter upon insulin stimulation (see e.g., FIG. 1).

Figure 3:
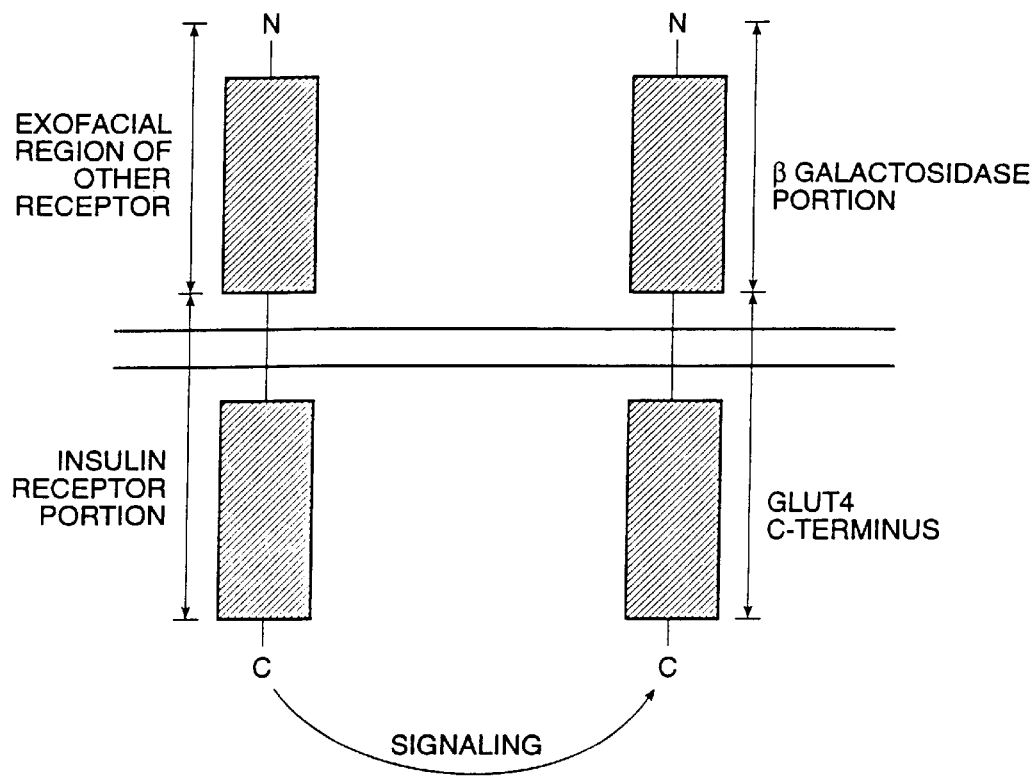

Another aspect of the invention involves the use of a chimeric insulin receptor system with a detectably-tagged chimeric GLUT transporter (see e.g., FIG. 3). Thus, fusion genes encoding chimeric receptor proteins can be constructed which include the extracellular portions of a receptor of interest and the transmembrane and cytoplasmic portions of the insulin receptor (see e.g., Ullrich et al. and Schlesinger et al.,). Accordingly, the cytoplasmic signaling domain of one receptor, e.g., the insulin receptor, can be activated by the ligand for another receptor when the exofacial portion of that latter receptor is joined to the former in a chimera receptor structure. Cells expressing chimera receptors where the cytoplasmic protein is the insulin receptor and the extracellular portion is a different receptor would respond to a ligand for the latter with increased glucose transporter translocation to the cell surface. Examples of receptor exofacial domains that could be fused with the β subunit portion of the insulin receptor include, without limitation, the EGF receptor tyrosine kinase, the PDGF receptor tyrosine kinase, the FGF receptor tyrosine kinase, the CSF receptor tyrosine kinase, IL-2, IL-4, IL-6, activin receptor and transforming growth factor receptors, and growth hormone receptor. Thus, the invention includes cells in culture or cells from transgenic animals containing both a reporter GLUT transporter construct of the type described in the above paragraph as well as a chimera insulin receptor (FIG. 3).

Polypeptide Expression

Polypeptides according to the invention may be produced by transformation of a suitable host cell with all or part of a chimeric GLUT transporter-encoding cDNA fragment (e.g., the cDNAs described above), or a portion of a GLUT transporter (e.g., the intracellular retention signal or the overexpression domain) in a suitable expression vehicle.

Those skilled in the field of molecular biology will understand that any of a wide variety of expression systems may be used to provide the recombinant GLUT transporter protein. The precise host cell used is not critical to the invention. The chimeric GLUT transporter may be produced in a prokaryotic host (e.g., *E. coli*) or in a eukaryotic host (e.g., *Saccharomyces cerevisiae* or mammalian cells, e.g., COS 1, NIH 3T3, and JEG3 cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1989). The method of transfection and the choice of expression vehicle will depend on the host system selected. Transformation and transfection methods are described, e.g., in Ausubel et al. (*Current Protocols in Molecular Biology*, John Wiley & Sons, New York, 1989); expression vehicles may be chosen from those provided, e.g., in *Cloning Vectors: A Laboratory Manual* (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promoter, an SV40 origin of replication which allows replication in mammalian systems, a selectable neomycin gene, and SV40 splicing and polyadenylation sites. DNA encoding a chimeric GLUT transporter would be inserted into the pMAMneo vector in an orientation designed to allow expression. The recombinant transporter protein would be isolated, if desired, as described below.

Other preferable host cells which may be used in conjunction with the pMAMneo expression vehicle include COS cells and CHO cells (ATCC Accession Nos. CRL 1650 and CCL 61, respectively).

Alternatively, a chimeric GLUT transporter is produced by a stably-transfected mammalian cell line. Cells expressing detectably-tagged chimeric GLUT transporter proteins are used, e.g., to screen for antagonists which disrupt an insulin receptor interaction or agonists which mimic an insulin receptor interaction (infra). Additionally, cells expressing detectably-tagged chimeric GLUT transporter proteins are used, e.g., to screen for antagonists which disrupt a chimeric insulin receptor interaction or agonists which mimic an chimeric insulin receptor interaction (infra).

A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the chimeric GLUT transporter is cloned into an expression vector which includes the dihydrofolate reductase (DHFR) gene. Integration of the plasmid and, therefore, the chimeric GLUT transporter-encoding gene into the host cell chromosome is selected for by inclusion of 0.01–300 $\mu$M methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

Once the recombinant GLUT transporter is expressed, it is isolated, e.g., using affinity chromatography. In one example, a binding site (e.g., the HA agglutinin epitope site infra) or an anti-GLUT transporter antibody (e.g., an antibody produced according to standard methods known in the art) may be attached to a column and used to isolate the receptor polypeptide. Lysis and fractionation of chimeric GLUT transporter-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short GLUT transporter fragments, e.g., the 30 amino acid GLUT4 retention signal (see FIGS. 11 and 12), can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful GLUT transporter fragments or analogs (described below).

Screening for Insulin Receptor or Chimeric Insulin Receptor Agonists (or Mimics) and Antagonists As discussed above, one aspect of the invention features screening for compounds that agonize the interaction between insulin and the insulin receptor (or between a chimeric insulin receptor such as a chimeric EGF:insulin receptor supra) cascade of events that are normally mediated by that interaction.

This screen requires recombinant cells expressing a suitable chimeric GLUT transporter (or a suitable transporter fragment or analog, as outlined above) configured to permit detection of binding. In one example, a candidate agonist is added to the NIH 3T3 cells stably expressing recombinant transporter (e.g., 1(1-53)/4 and 12CA5 antibody levels are measured (infra). An agonist or mimic useful in the invention is one which imitates the normal insulin-mediated signal transduction pathway, e.g., one which promotes an increase in expression of GLUT transporter levels. Alternatively, the screen requires recombinant cells expressing both a suitable chimeric GLUT transporter (or a suitable transporter fragment or analog, as outlined above) and a chimeric insulin receptor (as described supra, e.g., an EGF-:insulin chimera or an IL-6:insulin chimera) configured to permit detection of binding. In one example, a candidate agonist is added to the NIH 3T3 cells stably expressing both the recombinant GLUT transporter (e.g., 1(1-53)/4) and the chimeric EGF:Insulin receptor, and HA agglutinin levels are measured (as infra). An agonist or mimic useful in the invention is one which imitates the normal insulin-mediated signal transduction pathway upon stimulation of the extracellular EGF receptor portion, e.g., one which promotes a increase in expression of GLUT transporter levels.

Accordingly, any candidate antagonist compound may be assayed by any standard method, e.g., by contacting cell with insulin and the candidate antagonist and monitoring the induction of a chimeric GLUT transporter polypeptide. An antagonist useful in the invention is one which reduces the normal insulin-mediated signal transduction pathway upon stimulation of the insulin pathway, e.g., one which promotes a decrease in expression of GLUT transporter levels. Similarly, a candidate antagonist to any receptor could be evaluated using the insulin receptor chimeras describe supra. Again, an antagonist in the invention is one which reduces the normal insulin-mediated signal transduction pathway upon stimulation of the extracellular receptor portion of the insulin receptor chimera, e.g., one which promotes a decrease in expression of GLUT transporter levels.

Binding Studies

Knowledge that the 30 amino acid C-terminal domain of GLUT4 is a targeting signal to retain GLUT4 in an intracellular compartment suggests that such sequence is responsive to insulin and, therefore, provides a potential drug target. The use of the GLUT4 C-terminal sequence or a bacterial fusion protein containing this sequence for the purpose of screening compounds that have the capability of binding the GLUT4 C-terminal sequence could lead to identifying such a compound. In one example for identifying compounds that bind to the 30 amino acid C-terminal domain, the portion of the GLUT4 C-terminal region may be immobilized by reacting a synthesized polypeptide (supra) with a support, e.g., agarose. The intracellular retention signals (FIGS. 11 and 12) compounds of the invention are based upon the biologically active subfragment of the GLUT4 COOH-terminus. The symbols $A^x$(e.g., $A^1$) and the like; and Ser, Leu and the like, as found in a peptide sequence infra, stands for amino acid residues, e.g., =N—CH(R)—CO— when it is at the N-terminus, —CH(R)—COOH when it is at the C-terminus, or —NH—CH(R)— when it is at any other position. For example, R is —CH$_2$COOH for Asp, R is —H for glycine and R is —CH$_2$OH for Ser. When an amino acid residue is optically active, it is the L-form configuration that is intended unless the D-form is expressly designated. All amino sequences mentioned herein are written according to usual convention whereby the N-terminal amino acid is on the left and the C-terminal amino acid sequence is on the right. A short line between two amino acid residues indicates a peptide bond. The conventional abbreviations for the various amino acids are used.

Alternatively, a fusion protein containing the C-terminal region of GLUT4 can be immobilized on a support, e.g., agarose beads. Ordinarily, the compounds to be screened are reacted with the immobilized peptide, and the unreacted material washed away. Upon analysis of compounds that bind to the C-terminal peptide region of GLUT4, compounds could be isolated that have high binding affinities. Such compounds could then be tested for the ability to compete with the endogenous receptor for this C-terminal GLUT4 peptide by using the cell systems described above (e.g., 3T3-L1 or L6 myotubes) that harbor the exofacial HA-epitope tag GLUT4 or chimeric constructs. Compounds that render an HA-tagged GLUT transporter protein to move to the cell surface are potential drug candidates.

The results presented below demonstrate the effectiveness of the invention based on the insertion of a nine amino acid residue hemagglutinin (HA) epitope in the exofacial loop of glucose transporter proteins. This is accomplished, as described supra, by engineering DNA encoding this epitope into native and GLUT1/GLUT4 chimera constructs, expressing the tagged chimera proteins in COS-7 or CHO cells, and monitoring the binding of high affinity anti-HA epitope antibody to these fixed, non-permeabilized cells. Data obtained by this new method, as well as by the usual immunofluorescence microscopy techniques, reveal that the major determinant of glucose transporter localization to cell surface versus intracellular membranes resides in the unique COOH-terminal cytoplasmic sequences of the transporter proteins.

Methods

Cell Culture

COS-7 and CHO-K1 cells were obtained from American Type Culture Collection (Rockville, Md.). Media, trypsin, antibiotics, and G418 were from GIBCO/BRL (Gaithersburg, Md.) and FBS was purchased from Upstate Biotechnology, Inc. (Lake Placid, N.Y.). COS-7 cells were maintained in DME with 10% FBS, 50 U/ml penicillin, and 50 mg/ml streptomycin in a 37° C. humidified $CO_2$ incubator. The cells were subcultured before reaching confluence. CHO-K1 cell lines were maintained in Ham's F-12 medium with 10% FBS, 50 U/ml penicillin, and 50 mg/ml streptomycin in a 37° C. humidified $CO_2$ incubator.

Construction of HA-tagged Chimera Transporters

The cloning of the HepG2, GLUT1 cDNA was described previously (Harrison et al. 1990, J. Biol. Chem. 265:5793–5801). The full-length cDNA for GLUT4 was cloned from a rat skeletal muscle cDNA library (see, e.g., Ausubel et al., supra). All initial constructions were carried out in pUC18 or pUC19.

The construction of untagged chimeras was undertaken in a similar manner to the construction of chimeras 1(1-199)/4 and 1(1-462)/4 described previously 1990, J. Biol. Chem. 266:20213–20217). Convenient existing restriction sites were used to switch domains between the two transporter isoforms whenever possible. When existing restriction sites could not be found, new ones were made by site-directed mutagenesis such that the amino acid sequence was not altered. All of the constructions were confirmed by sequencing through the changed areas. The HA tag was inserted in the $NH_2$ terminus or exofacial loop of GLUT1 and GLUT4 using oligonucleotides encoding the sequences detailed below and having convenient restriction sites on the ends such that the tag could be inserted at the desired position in the protein. When necessary, HA tag insertions were carried out in subcloned fragments of the cDNA and the full length regenerated after insertions of the tag was confirmed by sequencing. Once the tag was inserted in the exofacial loop of the wild type transporters, these domains were swapped appropriately with the corresponding domains of the untagged chimera transporters to generate exofacially tagged chimeras. All tagged chimera transporters were cloned into the expression vector PCMV.

GLUT1N has the sequence YPYDVPDYA (SEQ ID NO:3) inserted after the first methionine. GLUT4N has the sequence AYPYDVPDYA (SEQ ID NO: 2) inserted after the first methionine. Exofacially tagged chimera transporters containing GLUT1 sequences in the $NH_2$ terminus have the sequence IDYPYDVPDYA (SEQ ID NO: 1) inserted between amino acids 53 and 54, in the predicted first exofacial loop. Transporters with GLUT4 $NH_2$ termini have the sequence IDYPYDVPDYA (SEQ ID NO: 1) inserted between amino acids 83 and 84. Domain switches were detailed in the legend of FIG. 4.

The construct 1(1-462)/4LL was made in the following manner. Oligonucleotides corresponding to the amino acids 480–509 of GLUT4 containing the mutations to change L489 and L490 to alanine residues were synthesized. The double stranded oligonucleotide fragment was cloned into the BglII-SalI site of the original 1(1-462)/4 construct in pUC19. The mutated construct was then transferred to the expression vector pCMV5. Construct 1(1-462)/4Y was made by truncating the original 1(1-462)/4 construct at amino acid 503 in the following way. A double stranded oligonucleotide corresponding to amino acids 480–503 of GLUT4 was inserted at BglII and SalI of the original 1(1-462)/4 construct in pUC19. The new construct was transferred to pCMV5.

Transient Expression of HA-Epitope-tagged Chimera Transporter cDNAs in COS-7 Cells COS-7 cells were seeded at 100,000 cells per 22-mm round glass coverslip and transfection of HA epitope-tagged chimera transporter cDNAs was performed by the calcium phosphate precipitation method as described (Gorman, 1985. In DNA Cloning. D M Glover, ed., IRL Press, Oxford, Vol II, 143–190)) or by the use of the lipofection reagent DOTAP (Boehringer Mannheim Biochemicals) according to the recommended protocol. Cells were analyzed by immunofluorescence 48 h later.

Stable Expression of Chimera transporter cDNAS in CHO-K1 Cells

Subconfluent CHO-K1 cells were co-transfected with pRSVneo and chimera transporter cDNAs by the calcium phosphate method described. G-418 resistant colonies were picked with the use of cloning cylinders and expanded. Positive cell lines were identified using immunofluorescence with anti-HA or anti-GLUT4 antibodies. Expression was confirmed by Western blotting of total cellular membranes.

Immunofluorescence of Transfected Cells

Forty-eight hours after transfection, COS-7 cells were washed three times in PBS (171 mM NaCl, 10 mM $Na_2HPO4$, 3.3 mM KCL, 1.8 mM $KH_2PO4$) fixed for 10 minutes at room temperature in 4% formaldehyde in PBS and rewashed three times in PBS. The fixed cells were then incubated with PBS containing 1% FBS and anti-HA antibody (mouse monoclonal 12CA5; BAbCO) diluted 1:1,000, for 2–3 h at room temperature. The cells were washed and bound primary antibody was detected with FITC-coupled goat anti-mouse IgG for 30 minutes at room temperature. After washing, the cells were postfixed with 4% formaldehyde in PBS for 5 minutes at room temperature. Cells were then permeabilized by incubating with PBS containing 1% FBS and 0.5% Triton X-100 for 30 minutes at room temperature. Cells were then incubated with a 1:1,000 dilution of either rabbit anti-GLUT4 IgG (R1288) or monoclonal anti-HA antibody (12CA5) depending on the COOH-terminal structure of the chimera for 18 h at 4° C. The cells were again washed, and bound primary antibodies detected with a 1:1,000 dilution of rhodamine-coupled goat anti-rabbit or anti-mouse IgG (Tago, Inc., Burlingame, Calif.). The cells were thoroughly washed and the coverglasses were mounted in 90% glycerol+2.5% DABCO.

Samples were then visualized on a microscope (IM-35; Carl Zeiss, Oberkochen, Germany), using a Nikon Apo 60/1.4 oil immersion lens. Images were recorded using a thermoelectrically cooled charged-couple device camera (Photometrics Ltd., Tucson, Ariz.). CHO-K1 cells were analyzed by immunofluorescence essentially as described above, except that the cells on coverslips were permeabilized directly after fixation and total cellular staining was detected with anti-HA antibody or anti-GLUT4 antibody (R1288) as necessary. Primary antibodies were detected with FITC-conjugated goat anti-mouse or goat anti-rabbit second antibodies as above.

Iodination of HA Antibody

Monoclonal antibody (12CA5) purchased from Babco and IgG fraction was purified according to standard methods. 75 $\mu$g of the anti-HA IgG was iodinated using a lactoperoxidase kit (ICN) according to manufacturer's instructions.

Iodinated Antibody Uptake

Cells were grown to 80% confluence in 24 well dishes. Cells were equilibrated in Buffer A (serum-free F12 media) for 30 minutes at 37° C. The buffer was then replaced with ice-cold Buffer A containing 30 $\mu$g/ml anti-HA IgG and $10^6$ cpm of $^{125}$I-anti-HA IgG. The plates were incubated at 4° C. for 1 hour, then washed several times with ice-cold Buffer A. The cells were then incubated with Buffer A at 37° C. for 2–10 minutes. Surface bound antibody was eluted in two sequential two minute washes with acidic buffer (100 mM Glycine, 20 mM Magnesium Acetate, 50 mM Potassium Chloride, pH 2.2). The two washes were saved and pooled, and cell monolayers were solubilized in 1% SDS. The radioactivity present in the acid labile and resistant pools was measured by gamma counting.

Antibody Uptake Detected with Immunofluorescence

Cells grown on glass coverslips were equilibrated at 37° C. for 30 minutes in Buffer A. The buffer was aspirated and replaced with fresh Buffer A containing 30 $\mu$g/ml anti-HA IgG for 10 or 60 minutes. The cells were then washed with ice cold PBS and fixed in 4% formaldehyde for 10 minutes. The cells were permeabilized for 1 minutes in room temperature methanol and briefly air dried. The fixed cells were incubated in PBS+1% FBS for 15 minutes, then incubated with a 1:1,000 dilution of FITC-coupled anti-mouse secondary antibody in the same buffer for 30 minutes. After several washes with PBS+1% FBS, the cells were postfixed in 4% formaldehyde for 10 minutes. Total expressed transporter was detected with a 1:1,000 dilution of anti-HA-GLUT4 (R1288) antibody, washed in PBS+1% FBS, and bound antibodies detected with a 1:1,000 dilution of Rhodamine coupled anti-mouse (anti-Ha) or anti-rabbit (GLUT4). Following extensive washes with PBS+1% FBS, the coverslips were mounted on slides using 90% glycerol+ 2.5% DABCO.

Antibody and Transferrin Uptake

Cells grown as described above were assayed similarly except that 2.5 $\mu$g/ml Texas Red labeled transferrin was included in the incubation. Internalized antibody was detected with FITC-coupled anti-mouse antibody as above. Total expression was not measured in these experiments.

2-Deoxyglucose Uptake

Cells were assayed for 2-deoxyglucose uptake according to standard methods (see e.g., Harrison et al., (1990) *J. Biol. Chem.*, 265:5793–5801). Nonspecific uptake, measured in the presence of 20 $\mu$M cytochalasin B and 300 $\mu$M phloretin, was subtracted and the cpm were normalized per $10^5$ cells.

Digital Imaging Microscopy

Samples were visualized on a Zeiss IM-35 microscope using a Nikon Apo 60/1.4 oil immersion lens and an 8× eyepiece. Two-dimensional images were recorded using a thermoelectrically cooled charge-coupled device camera (Photometrics Ltd.). To determine co-localization of signals, a powerful deconvolution algorithm that reverses the blurring introduced by the microscope optics was used. For these experiments, 30 serial two-dimensional images were recorded at 0.25 $\mu$M intervals. Each image was corrected for lamp intensity variations and photobleaching. Blurring of fluorescence from regions above and below the plane of focus was reversed using an iterative constrained deconvolution algorithm based on the theory of ill-posed problems.

Results

Exofacial Epitope-tagged GLUT1 is Bound by Antibody 12CA5 in Intact Cells

Figure 4:
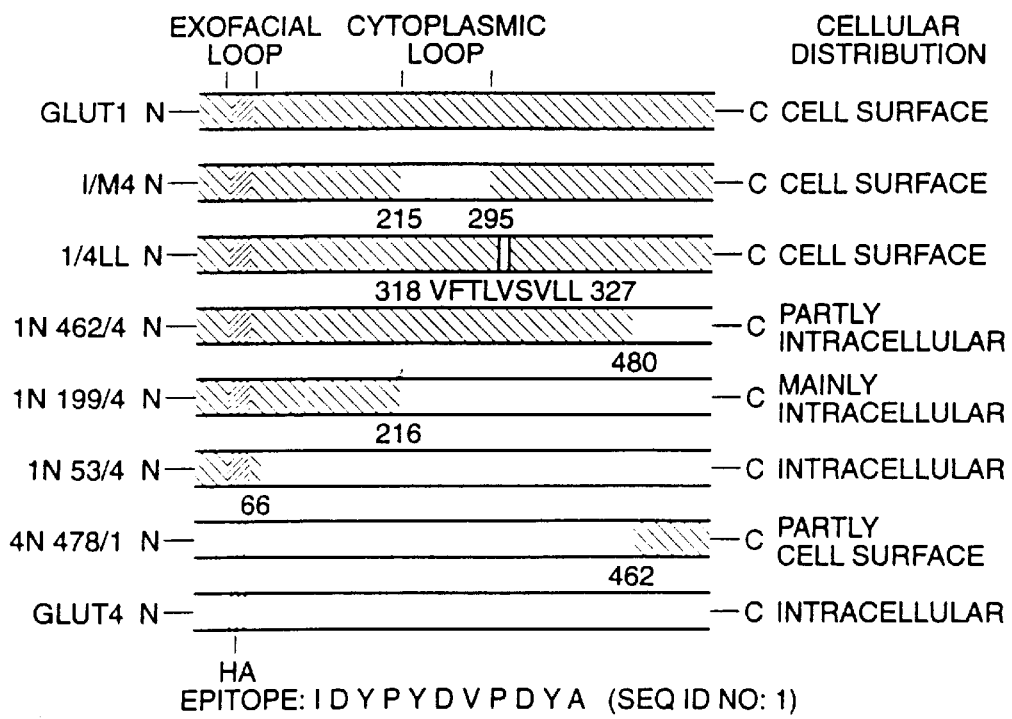

As a means of assessing the concentrations of glucose transporters at the cell surface membrane, we devised a strategy to confer a known antibody recognition site on the predicted exofacial loops of these proteins. To achieve this objective, cDNA constructs encoding HA-tagged GLUT1, GLUT4, and the GLUT1/GLUT4 chimera transporters were prepared as depicted schematically in FIG. 4. DNA encoding the nine amino acid HA epitope sequence YPYDVPDYA was inserted into the GLUT1 exofacial loop or into the GLUT4 exofacial loop. Chimera GLUT1/GLUT4 cDNA constructs containing these exofacial loop HA inserts were then engineered as indicated. In addition, GLUT1 and GLUT4 constructs were then prepared containing HA epitope tags at their NH$_2$ termini, which are predicted to extend into the cytoplasmic domain (GLUT1N AND GLUT4N in FIG. 4). The cDNA constructs were then ligated into the expression vector pCMV and expressed in COS-7 cells (see FIGS. 5–9). Some of these constructs were also stably transfected into CHO cells (see FIG. 9). Insertion of the HA epitope into the GLUT1 structure at either the NH$_2$ terminus or exofacial loop did not disrupt function because CHO cells overexpressing these proteins exhibited the expected increase in glucose transport activity. FIG. 4 summarizes the cellular distributions observed with these expressed constructs, as described in detail below.

Figure 5:
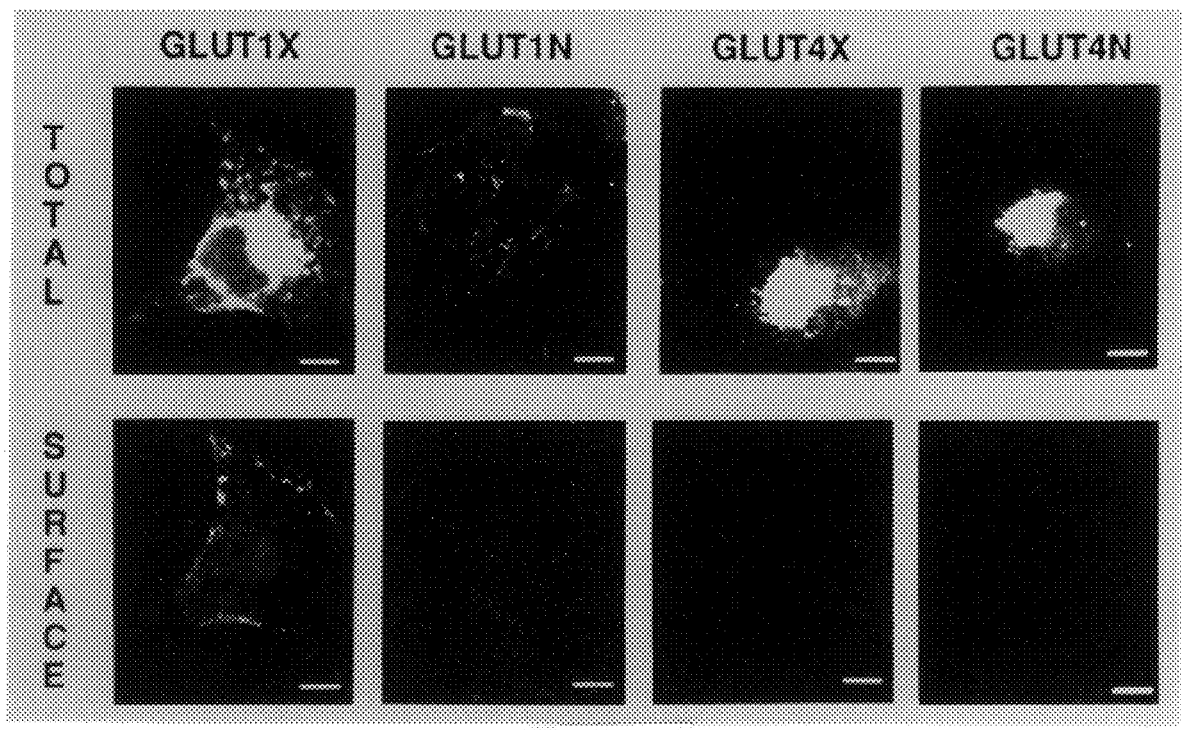

The HA-tagged glucose transporter proteins depicted in FIG. 4 were transiently expressed in COS-7 cells. The cell surface concentration of each construct was analyzed by immunofluorescence microscopy of non-permeabilized cells using a monoclonal anti-HA epitope antibody (12CA5) followed by a FITC-coupled anti-mouse secondary antibody. Subsequently, the cellular localizations of all expressed transporters in the same cells was determined by permeabilization with 0.5% Triton X-100, a second exposure to the same primary antibody, and then incubation with a rhodamine-coupled anti-mouse secondary antibody. FIG. 5 shows the expected divergent cellular disposition of the NH$_2$-terminal (GLUT4N) and exofacial (GLUT4X)

HA-tagged native GLUT4 vs. the NH$_2$-terminal GLUTIN) and exofacial (GLUTIX) HA-tagged native GLUT1 in fixed, permeabilized COS-7 cells (top). GLUT4N and GLUT4X exhibit a highly concentrated perinuclear localization, whereas GLUTIN and GLUTIX are readily detected at the cell border as well as in the perinuclear region. These patterns of distribution were identical to those observed with native, untagged GLUT4 and GLUT1, detected with their respective anti-COOH terminal peptide antibodies, following expression in COS-7 cells.

To directly determine the levels of expressed transporter proteins on the cell surface, binding of anti-HA epitope antibody to non-permeabilized COS-7 cells was examined. The results showed that exofacial HA epitope-tagged GLUTIX was readily detected under these non-permeabilized conditions (FIG. 5, bottom) in the same cells found to express this protein by labeling after permeabilization (FIG. 5, top). No signal was observed in non-permeabilized COS-7 cells expressing the GLUT4N, GLUT1N, or GLUT4X, as predicted by either the cytoplasmic disposition of the HA tag (GLUT4N and GLUT1N) or by the intracellular localization of the transporter proteins (GLUT4X). Taken together, these results confirm the utility of this experimental strategy using exofacial HA epitope tagging to determine the cell surface localization of glucose transporters.

Figure 6:
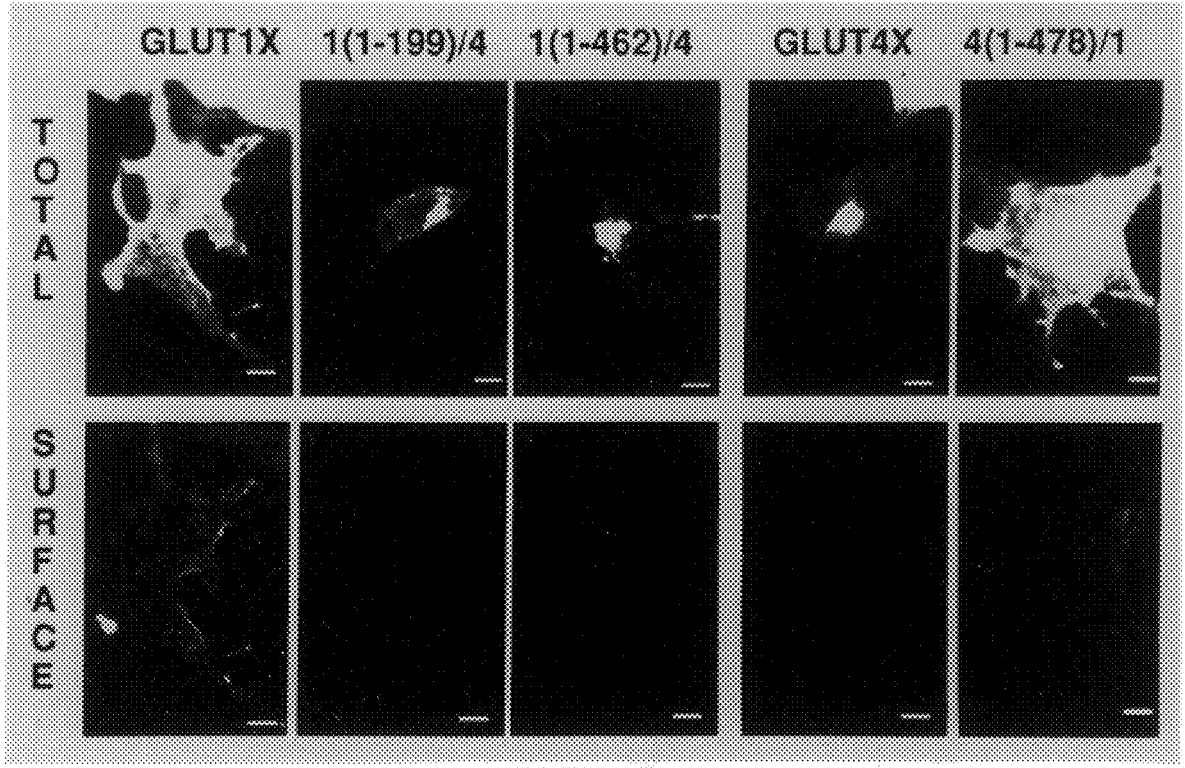

The Variable COOH-terminal Cytoplasmic Domain is a Major Determinant of Glucose Transporter Localization Using the above methodology, the extent to which the extreme COOH-terminal sequences on the glucose transporters influenced cellular localization was evaluated. Continuing from the last COOH-terminal membrane spanning segment, the first 11 amino acid residues of the predicted COOH-terminal cytoplasmic tails of GLUT1 and GLUT4 are highly similar (approximately 80% sequence identity), whereas the remaining COOH-terminal tail residues are quite dissimilar (approximately 20% sequence identity). These divergent COOH-terminal residue segments on the GLUT1 and GLUT4 proteins have been switched in constructs 4(1-478)/1 and 1(1-462)/4 (see FIG. 4). In this series of experiments, the exofacial HA-tagged GLUTIX and GLUT4X also displayed the usual cell surface and perinuclear dispositions, respectively (FIG. 6). Remarkably, substituting the COOH-terminal 30 amino acids of GLUT4 onto GLUT1 (1[1-462]/4) caused a perinuclear localization of the chimera, as visualized in permeabilized cells (FIG. 6, top). When non-permeabilized COS-7 cells were analyzed with the 12CA5 antibody, GLUTIX-expressing cells were readily observed, whereas no signal above background was detected in cells expressing the 1(1-462)/4 glucose transporter construct (FIG. 6, bottom). Chimera 1(199)/4 containing the NH$_2$ terminal 199 residues of GLUT1 and the remaining COOH-terminal residues of GLUT4 also exhibited an intracellular localization when expressed in COS-7 cells.

A chimera in which the 29 COOH-terminal residues of GLUT1 were substituted onto GLUT4 (4[1-478]/1) confirmed the importance of the variable COOH-terminal sequences of GLUT1 and GLUT4 in determining whether these proteins distribute significantly to the plasma membrane. Thus, the 4:1-478)/1 protein was readily observed when analyzed in non-permeabilized COS-7 cells with the 12CA5 antibody (FIG. 6, bottom), and displayed an overall distribution pattern that resembled native GLUT1 when visualized in permeabilized cells (FIG. 6, top). Comparison of the intensity of cell surface staining of GLUTIX vs 4(1-478)1 at similar levels of total transporter expression indicated the former achieves a higher concentration at the cell surface. This suggests that other structural elements may also play a significant role in glucose transporter membrane distribution. Taken together, the data in FIG. 6 reveal a heretofore unrecognized major cell localization determinant in the COOH-terminal region of the GLUT1 and GLUT4 transporter proteins.

A Transporter Domain between the Exofacial and Extracellular Loops Influences Cellular Localization We then tested whether the extent of total glucose transporter protein expression in COS-7 cells might influence the apparent cellular localization of transporters. The presently developed methodology allows us to rigorously compare both total expression levels of transporters and the concentration of these proteins on the cell surface.

Figure 7:
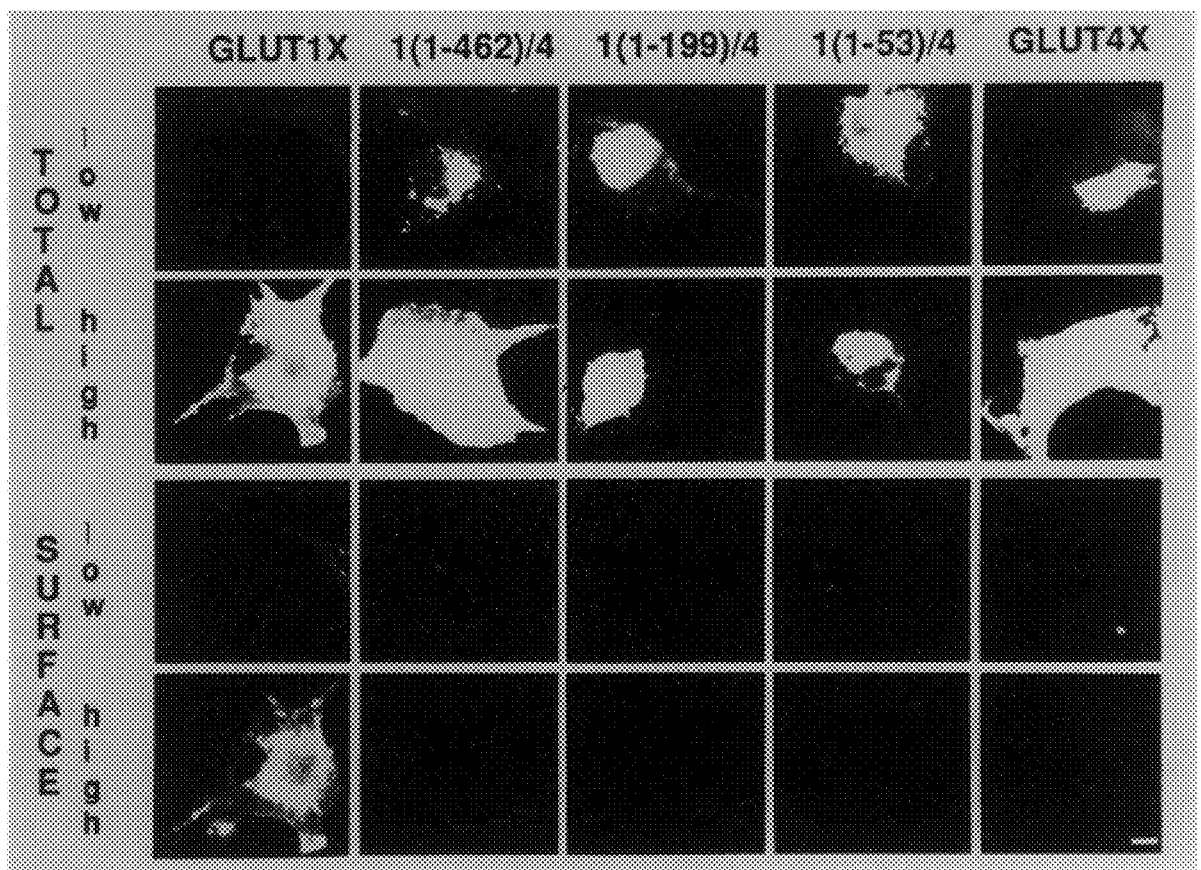

FIG. 7 depicts the results of experiments in which the cell surface concentration of transporters was analyzed in COS-7 cells expressing either high or low amounts of total heterologously expressed transporter protein. Cells were chosen based on their immunofluorescence intensity after permeabilization and staining with 12CA5 and rhodamine-tagged anti-mouse Ig. The cell surface concentration of HA-tagged transporter was then determined by visualizing fluorescence from the FITC-labeled anti-Ig antibody, which reflects the anti-HA antibody bound to cells before permeabilization. COS-7 cells expressing low amounts of HA-tagged transporter protein showed completely intracellular distributions of GLUT4X (1[1-462/4, 1[1-199/4, or 1[1-53/4]), as assessed by the lack of FITC staining. In contrast, cell surface GLUTIX was readily observed under these conditions (FIG. 7, panels SURFACE, low). The results confirm those of FIG. 6, and reinforce the lack of detectable influence of extreme NH$_2$-terminal sequences in governing intracellular localization (constructs 1[1-53]/4 vs. GLUT4X).

In contrast, similar analysis of COS-7 cells expressing high concentration of these constructs revealed the presence of chimeras 1(1-464)/4 and 1(1-199)/4 on the cell surface, but not of 1(1-53)/4 or GLUT4X (FIG. 7, panels SURFACE, high). These results indicate that GLUT4 sequences of 66-216 or the corresponding region of GLUT1, contain structural elements that may also play a role in the cellular localization of GLUT1 and GLUT4. In these present experiments, the influences of these sequences only becomes evident at high levels of glucose transporter expression.

Figure 8:
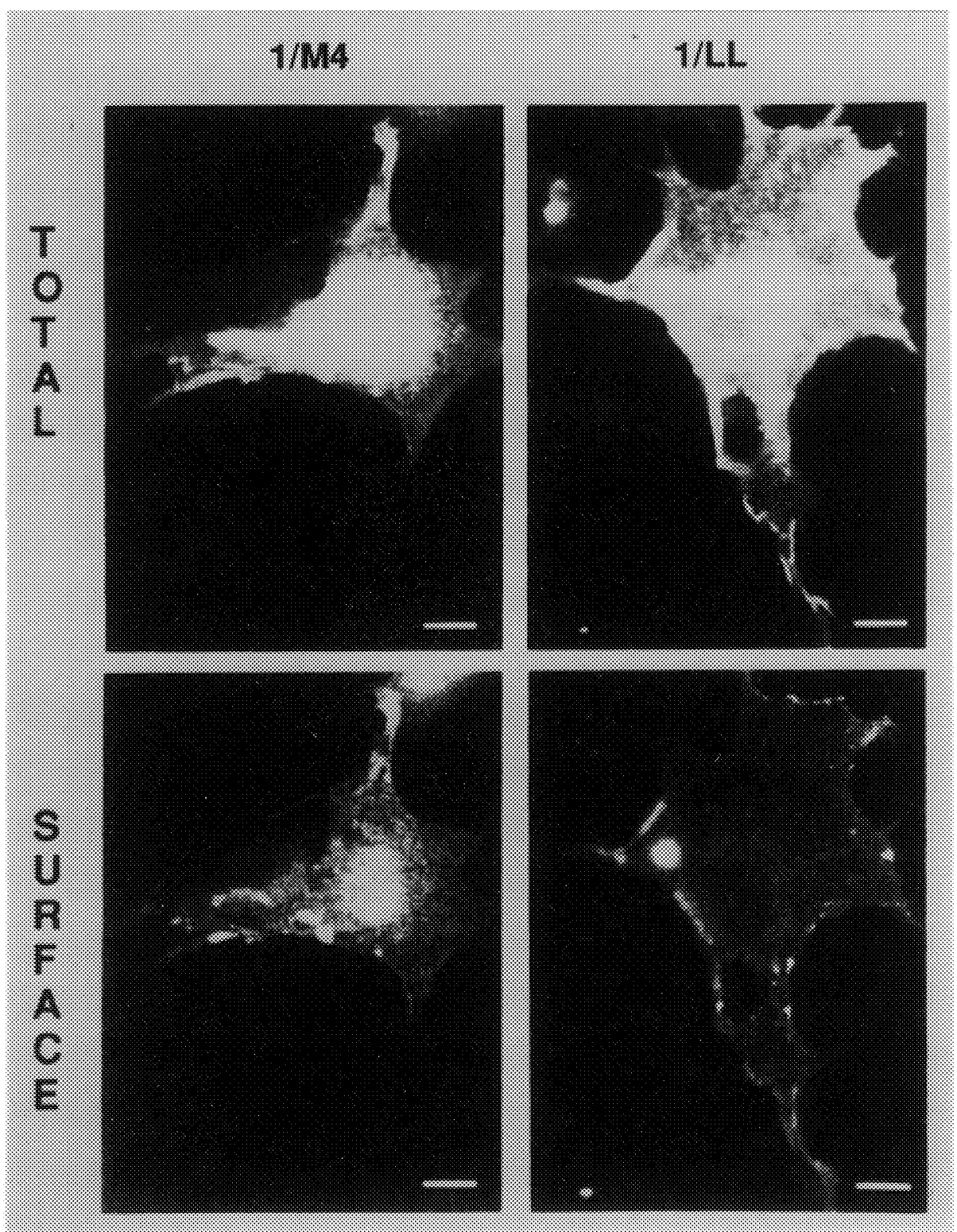

The analysis depicted in FIG. 7 shows that the extreme NH$_2$-terminal residues of GLUT4 fail to effect membrane distribution of this transporter protein. Experiments were also undertaken to examine the possible influence of the major GLUT4 intracellular loop on cellular localization of glucose transporters. A GLUT1 construct (1/M4) with this GLUT4 middle loop substitution was expressed in COS-7 cells and found to distribute in a manner identical to native GLUT1 when probed with 12CA5 antibody following fixation and permeabilization of the cells (FIG. 8, panel TOTAL). Cell surface display of this chimera was confirmed by detection of intense fluorescence images when non-permeabilized COS-7 cells were analyzed (FIG. 8, panel SURFACE). Similar findings were made using a GLUT1 construct (see 1/4LL construct in FIG. 4) in which the sequence of the seventh intracellular loop of GLUT1 was substituted for that of GLUT4 (FIG. 8). These results indicate that GLUT4 sequences present in the fifth and seventh intracellular loops do not appear to influence transporter localization.

GLUT4 COOH-terminal Domain Also Confers a Perinuclear Localization in CHO Cells

Figure 9:
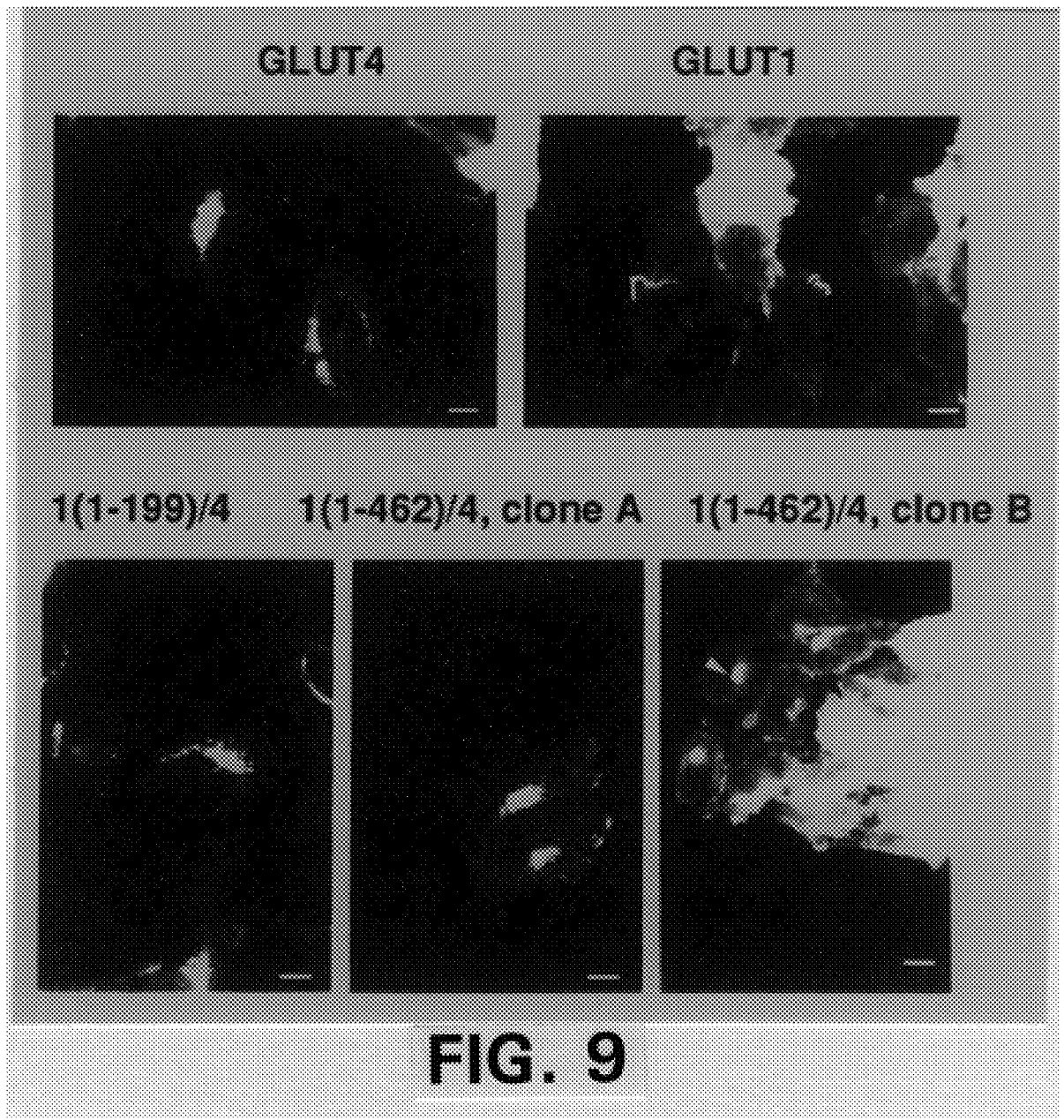

In the following studies CHO cells were stably transfected with native GLUT1, GLUT4 constructs, GLUT1X and GLUT4N, chimera 1(1-199)/4 depicted in FIG. 4 in order to evaluate role of the COOH-terminal tail domain of transporter proteins in membrane trafficking. Stably transfected cell lines expressing a chimera 1(1-462)/4 containing GLUT1 sequences except for the 30 amino acid COOH-terminal GLUT4 domain substitution (as in FIG. 4 but without the HA tag) were also developed. Analysis of GLUT4N and chimera 1(1-199)/4 localization with 12CA5 antibody in the transfected CHO cells after fixation and permeabilization showed a marked perinuclear concentration (FIG. 9), similar to that observed for these transporters in COS-7 cells (FIGS. 5–7). Interestingly, GLUT1X displayed a distribution pattern that was almost exclusively localized to the cell periphery, with very little intracellular staining in these CHO cells (FIG. 9). In contrast, the 1(1-462)/4 chimera composed of GLUT1 sequences except for the extreme 30-residue GLUT4 COOH-terminal substitution displayed an intracellular, perinuclear distribution. Interestingly, at high levels of expression, this transporter chimera was also detected at the cell surface. These results define the variable COOH-terminal domain of these transporters as a critical determinant of cellular localization.

In summary, insertion of the HA epitope into the predicted exofacial loops of GLUT1 and GLUT4 as a means of monitoring exposure of the tagged transporters to the extracellular space is documented by the present studies. This method provides unambiguous results, provided the surface membranes of the cells analyzed are intact and impermeable to anti-HA immunoglobulin added to the medium. Thus, exofacial loop-tagged GLUTIX is intensely stained with antibody on the surface of transfected, non-permeabilized COS-7 cells, whereas GLUT-1 containing the HA tag on its cytoplasmic $NH_2$ terminus (GLUTIN) is not visualized under these conditions. (FIG. 5). This latter construct serves as a valuable control for the possibility that processing cells in any given experiment permeabilizes the plasma membrane to anti-HA antibody. It should be noted that 12CA5 antibody binding to intact cultured cells can also be performed prior to fixation and analysis in order to assess cell surface transporters. Other advantages of this technique include the high affinity of the commercially available 12CA5 antibody and the ability to assess transporter localization following transient transfection, when only a small percentage of cells express the desired transporter construct.

The exofacial HA epitope-tagging method used here also reveals major limitations in the use of standard immunofluorescence microscopy for assessing cell surface proteins. Antibody staining in regions near the cell periphery can be easily mistaken for actual cell surface localization. For example, high levels of expression of chimera 1(1-53)/4 in permeabilized COS-7 cells causes intense staining with the 12CA5 antibody extending to areas along the plasma membrane (FIG. 7, panel TOTAL, high). However, in non-permeabilized COS-7 cells transfected with this construct, no cell surface binding to anti-HA antibody is detected. In contrast, 1(1-462)/4 transporter, which displays a similar staining pattern to 1(1-53)/4 in permeabilized COS-7 cells, is readily detected in non-permeabilized cells as well (FIG. 7). Thus, the HA-tagging method is able to document plasma membrane localization of transporter constructs even when this is difficult by the standard immunofluorescence microscopy techniques used by other investigators.

Finally, the present studies, designed to assess actual exposure of glucose transporter chimeras on the cell surface, have revealed the COOH terminus as a major structural determinant of transporter localization in COS-7 and CHO cells. Detecting the HA epitope of the 4(1-478)/1 chimera on the cell surface of non-permeabilized cells unequivocally confirmed the observations (FIGS. 6 and 7).

GLUT4 Intracellular Retention Sequence

In order to further define the role of the GLUT4 COOH-terminal 30 amino acid domain as a signal for intracellular localization, the present studies focused on glucose transporter chimeras in which this GLUT4 COOH-terminal domain is substituted onto GLUT1 (FIG. 12, Panel A [1]). The chimera denoted 1(1-462)/4 contains native sequences of human GLUT1 residues (1-462) and the rat GLUT4 COOH-terminus (residues 480-509), and has previously been shown to display a GLUT4-like perinuclear disposition when expressed in COS-7 or CHO cells (supra). Under similar experimental conditions, native GLUT1 is primarily a cell surface protein. Comparison of the amino acid sequences of the GLUT1 and GLUT4 COOH-terminal regions (FIG. 12, Panel B [1]) revealed a unique double leucine and tyrosine motifs. Based on this observation tested the significance of these motifs by engineering mutant chimera constructs in which the double leucines 489 and 490 were converted to alanines (construct 1(1-462)/4LL) or the GLUT4 COOH-terminus was truncated at position 503 so that tyrosine 504 is missing (construct 1(1-462)/4Y). Additionally, each of the constructs depicted in FIG. 12, Panel A were engineered to contain the HA epitope sequence YPYDVPDYA within the major exofacial loop. The native chimera (1(1-462/4) and double leucine mutant (1(1-462)/4LL) constructs depicted in FIG. 12 encode functional transporter proteins because their overexpression in stably transfected CHO cells confers several-fold increases in glucose transport activity to these cell lines.

GLUT4 Perinuclear Localization Requires the COOH-terminal Dileucine

In order to determine the steady-state cellular localization of native and mutant glucose transporter chimeras, the exofacial HA-tagged constructs depicted in FIG. 12, Panel A were transiently expressed in COS-7 cells (FIG. 13). The cell surface concentration of each construct was analyzed by immunofluorescence microscopy of non-permeabilized cells using a monoclonal anti-HA epitope antibody (12CA5) followed by a FITC-coupled anti-mouse immunoglobulin secondary antibody. Subsequently, the cellular localization of all expressed transporters in the same cells was determined by permeabilization with 0.5% Triton, an exposure to anti-GLUT4 or anti-HA antibody, and then incubation with a rhodamine-coupled anti-rabbit or anti-mouse immunoglobulin secondary antibody. That this procedure quantifies the cell surface complement of expressed transporters was previously verified by the finding that exofacial HA-tagged GLUT1, but not GLUT1 tagged at its cytoplasmic N-terminus, was readily detected by anti-HA antibody bound to nonpermeabilized cells (supra).

FIG. 13 shows that at similar levels of cellular expression, much higher levels of GLUT1X are detected at the cell surface compared to the 1(1-462)/4 construct, confirming our previous findings that the GLUT4 COOH-terminus confers an intracellular disposition. The marked perinuclear appearance of the 1(1-642)/4 chimera visualized in permeabilized cells (upper panel) resembles the results obtained with native GLUT4 (supra). Similar data are obtained when the 1(1-462)/4Y protein is expressed in COS-7 cells. In contrast, mutation of the double leucines in this construct to alanines (construct 1(1-452)/4LL in FIG. 12, Panel A) results in a large increase in the levels of transporter at the cell surface, as visualized by the intense signal from anti-HA antibody in nonpermeabilized cells (FIG. 13, lower panel), similar to GLUT1X. In permeabilized cells this mutant construct is distributed throughout the cell rather than restricted to the perinuclear region, again similar to the GLUT1X transporter protein (FIG. 13). Quantifications of the immunofluorescence intensities by digital image microscopy to obtain surface transporter content/total transporter ratios for GLUT1X, 1(1-462)/4 and 1(1-462)/4LL yielded the values of 0.51±0.08, 0.18±0.05, and 0.51±0.10, respectively. Taken together, these data indicate that the capability of the GLUT4 COOH-terminus to confer a steady-state intracellular localization when substituted onto the GLUT1X construct requires intact leucines 489 and 490.

The validly of this conclusion was tested using independent methodology in a different cell type. As depicted in FIG. 14, CHO cells stably transfected with GLUT1X, 1(1-462)/4 or 1(1-462)/4LL were fixed, permeabilized, and analyzed with anti-HA antibody and an anti-GLUT4 COOH-terminal peptide antibody. GLUT1X protein exhibited a dispersed pattern of anti-HA immunoreactivity, with high intensity at cell borders characteristic of its cell surface concentration. As expected, these same cells were devoid of anti-GLUT4 antibody-mediated immunofluorescence (FIG. 14, top panel). In sharp contrast, the chimera containing the native GLUT4 COOH-terminal region was largely restricted to a perinuclear localization when permeabilized cells were probed with either anti-HA. (lower panel) or anti-GLUT4 (top panel) antibodies. Again, mutation of the double leucines 489 and 490 to alanines caused reversion of this distribution to a GLUT1X-like, cell surface phenotype, as evidenced by probing with either antibody (FIG. 14). Quantification of data obtained from other experiments on CHO cells (not shown) for SURFACE/TOTAL values also confirmed similarly increased cell surface content of GLUT1X and 1(1-462)/4LL over 1(1-462)/4. These data demonstrate that the double leucine motif is a necessary element of the cellular localization signal in the GLUT4 COOH-terminus.

The GLUT4 COOH-terminal Dileucine Signals Rapid Endocytosis

In the next series of experiments, we took advantage of the fact that anti-HA antibody binds to exofacial-tagged transporter proteins in intact living cells. The ability of HA-tagged transporters to direct the internalization of antibody can be used as direct means of estimating transporter endocytosis. Transiently transfected COS-7 cells (FIG. 15) and stably transfected CHO cells (FIG. 16) expressing GLUT1X, chimera 1(1-462)/4, or the double leucine mutant chimera 1(1-462)/4LL were incubated with 12CA5 antibody at 37 for 10 or 60 minutes. Cells were then fixed, permeabilized and incubated with FITC-labeled anti-mouse immunoglobulin antibody to visualize the internalized monoclonal 12CA5 (panels labeled "10 min" and "60 min" in FIGS. 15 and 16). Distribution of total transporter proteins in the same fixed permeabilized cells were visualized by a subsequent incubation with anti-HA (for GLUT1X) or anti-GLUT4 (for chimeras) followed by rhodamine-conjugated anti-mouse or anti-rabbit immunoglobulin antibody (panels labeled "total" above the 10 min or 60 min panels, respectively). Time-dependent uptake of the anti-HA antibody directed by the glucose transporter proteins was observed in both COS-7 (FIG. 15) and CHO (FIG. 16) cells, but was much more pronounced with cells expressing the 1(1-462)/4 chimera compared to GLUT1X or the double leucine mutant chimera. In COS-7 cells, 12CA5 antibody uptake in GLUT1X or 1(1-462)/4LL expressing cells was virtually undetectable at 10 minutes, while the 1(1-462)/4 chimera mediated a relatively strong signal by this time (FIG. 15). By 60 minutes of incubation, cells expressing the 1(1-462)/4 chimera exhibited intense accumulation of the 12CA5 antibody in the perinuclear region as well as in punctate, peripheral structures. Mutation of the double leucines in this chimera abolished detectable uptake of the anti-HA antibody into the perinuclear region. No internalized antibody could be detected in non-transfected cells (not shown).

The significantly elevated rates of 1(1-462)/4 protein internalization observed in FIGS. 15 and 16 relative to those of GLUT1X and the mutant 1(1-462)/4LL chimera seemed particularly remarkable because much less of the former chimera protein is present on the cell surface at steady-state compared to the latter proteins (FIG. 13). Thus, a much smaller pool of surface bound 12CA5 antibody is available to be internalized in cells expressing the 1(1-462)/4 chimera compared to those expressing GLUT1X or 1(1- 462)/4LL (FIG. 12), even though in fact the former cells do internalize more 12CA5 antibody than the later (FIGS. 15 and 16). Using digital imaging microscopy, the fluorescence intensity associated with the newly internalized anti-HA antibody in COS-7 cells was quantified. When normalized to the calculated cell surface content of transporter protein, we obtained internalization values (anti-HA Uptake/Steady-state Cell Surface Transporter Content) for 1(1-462)/4 that were three times greater than GLUT1X and 1(1-462)/4LL at 10 minutes and over 10-fold greater at 60 minutes. Experiments were also conducted to quantify the 12CA5 antibody internalization rate relative to its steady-state cell surface binding using methodology previously established for comparison of receptor endocytosis rate (see, e.g., Davis et al., (1987) *J. Biol. Chem.*, 262:13126–13134). Antibody 12CA5 labeled with $^{125}$I was incubated with stably transfected CHO cells expressing transporter proteins GLUT1X, 1(1-462)/4 or 1(1-462)/4LL for 1 hour at 4° to bind cell surface transporters. Unbound antibody was washed away and cells were incubated at 37° for various times (2–10 minutes) to allow endocytosis to proceed. The amount of 12CA5 antibody remaining on the cell surface at each time point was removed by acid washing, and quantified. The amount of internalized radioactivity still associated with the cells was also determined.

The data obtained for each time of internalization in these experiments was plotted as a ratio of internalized 12CA5 antibody to cell surface bound antibody (In/Sur) in FIG. 17. About half of the initial surface bound 12CA5 antibody was already internalized within only two minutes of incubation at 37° when directed by the 1(1-462)/4 transporter chimera, and internalization continued to proceed rapidly through the 10 minutes incubation period. In contrast, the In/Sur ratio calculated for the GLUT1X containing cells was about 2-fold lower at 2 minutes and 5-fold lower at the 10 minutes time point (FIG. 17). Cells expressing the mutant chimera with the double leucines converted to alanines displayed a low internalization rate indistinguishable from that measured in GLUT1X-expressing cells. Taken together, the data presented in FIGS. 15–17 demonstrate that the steady-state perinuclear localization conferred by the 30 residue GLUT4 COOH-terminal domain when substituted onto GLUT1 is associated with an elevated rate of internalization compared to native GLUT1. Both of these functions are directed by the GLUT4 COOH-terminus, and are abolished upon mutation of the double leucine motif in the GLUT4 domain.

Newly Internalized and Total Cellular Chimera Transporters Co-localize

The results described above indicate that the GLUT4 COOH-terminus contains a signal for internalization, and suggests that the predominantly intracellular localization of GLUT4 is the result of efficient retrieval from the plasma membrane. However, an alternative possibility could be that GLUT4 is targeted to two different cellular compartments, one being the endocytic pathway and another being a specialized intracellular storage pool which keeps the transporter sequestered from the plasma membrane. To determine whether the pool of transporters that internalize antibody is separated from a non-recycling pool, we used digital imaging microscopy to assess rigorously the degree of co-localization of recycling vs. total cellular pools of transporters. Transfected COS-7 cells producing 1(1-462)/4 chimera protein were incubated with the anti-HA antibody for 60 minutes followed by washing, fixation, permeabilization and probing with FITC-anti-mouse immunoglobulin antibody. After this treatment, the same cells were incubated with anti-GLUT4 antibody followed by rhodamine-labeled anti-rabbit immunoglobulin antibody to visualize the cellular distribution of the total pool of chimera transporter proteins. Three dimensional images of the total pool of transporters (two representative fields visualized in red in left panels of FIG. 18) and of the fluorescein signal associated with transporters internalized during the 60 minutes incubation (visualized in green in the middle panels, of FIG. 18) were generated. Areas of co-localization of rhodamine-based and fluorescein-based signals observed after overlapping both images are displayed in white (right panels of FIG. 18).

Three important findings emerge from this analysis with First, the 1(1-462)/4 chimera protein in these cells appears as a distinct punctate pattern, suggesting its sorting into discrete vesicular structures (left panels). Second, while many of these chimera-containing structures are situated in the perinuclear region of the cells, they are clearly present throughout the cytoplasm. Third, newly internalized 1(1-462)/4 chimera proteins distributed within 60 minutes to most of the same vesicular structures that contain the bulk transporter protein pool (right panels of FIG. 18). These data are consistent with the hypothesis that most if not all of the 1(1-462)/4 chimera transporters are continually recycling between intracellular vesicular structures and the cell surface membrane in COS-7 cells.

Newly Internalized Chimera Transporters and Transferrin Co-localize

We then tested whether the 1(1-462)/4 chimera is internalized via the endocytic pathway through which transferrin receptor and other receptors are internalized. COS-7 cells expressing 1(1-462)/4 chimera were incubated simultaneously with Texas red-tagged transferrin and anti-HA antibody for 60 minutes at 37° C. Cells were fixed, permeabilized and primary 12CA5 antibody was detected with FITC-labeled anti-mouse immunoglobulin antibody. The same three dimensional reconstruction and co-localization of Texas red versus fluorescein based fluorescence analysis were performed as described above for FIG. 18. The data in FIG. 19 depicting two distinct fields (upper versus lower panels) show quite similar distribution profiles for the internalized transferrin (visualized in red in left panels) and anti-HA antibody (visualized in green in middle panels). Note that in the upper panels a single cell is visualized, whereas in the lower panels, multiple cells are present. Only one cell among the latter has been transfected with the chimera transporter cDNA, whereas all the cells contain endogenous transferrin receptors and internalized Texas red-labeled transferrin. Numerous vesicular structures harboring internalized transferrin also contain chimera transporter protein, as visualized in white in the right panels of FIG. 19.

Other Embodiments

Polypeptides according to the invention include the chimeric GLUT transporter polypeptides depicted in FIG. 4, FIG. 10 (SEQ ID NO: 5), FIGS. 11 and 12 (SEQ ID NO: 7), and SEQ ID NO: 8 as well as any analog or fragment of a chimeric GLUT transporter polypeptide, overexpression domain and intracellular retention signal (as constructed and identified using the techniques described supra).

Specific chimeric GLUT transporter polypeptide, overexpression domain and intracellular retention signal fragments or analogues of interest include full-length or partial (see below) polypeptides including an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the polypeptides ability to serve as a detectably-tagged polypeptide; or to promote overexpression and intracellular retention (as assayed supra). Analogs also include polypeptides which are modified for the purpose of increasing peptide stability; such analogs may contain, e.g., one or more desaturated peptide bonds or D-amino acids in the peptide sequence or the peptide may be formulated as a cyclized peptide molecule.

We claim:

1. A substantially pure DNA molecule consisting of a nucleotide sequence encoding a GLUT transporter intracellular retention signal, wherein the signal has the amino acid sequence of SEQ ID NO:7 or SEQ ID NO:8, or an intracellular retention signal fragment of SEQ ID NO:7 or SEQ ID NO:8 that signals a GLUT transporter polypeptide to remain within an intracellular compartment.

2. A substantially pure DNA molecule consisting of a nucleotide sequence encoding a GLUT transporter overexpression domain, wherein the domain has the amino acid sequence of SEQ ID NO:5, or an overexpression domain fragment OF SEQ ID NO: 5 that induces expression of a GLUT transporter polypeptide.

3. A substantially pure DNA molecule consisting of a nucleotide sequence encoding a GLUT transporter intracellular retention signal and a detectable heterologous polypeptide, wherein the signal has the amino acid sequence of SEQ ID NO:7 or SEQ ID NO:8, or an intracellular retention signal fragment of SEQ ID NO:7 or SEQ ID NO:8 that signals a GLUT transporter polypeptide to remain within an intracellular compartment.

4. A substantially pure DNA molecule consisting of a nucleotide sequence encoding a GLUT transporter overexpression domain and a detectable heterologous polypeptide, wherein the domain has the amino acid sequence of SEQ ID NO:5, or an overexpression domain fragment of SEQ ID NO:5 that induces expression of a GLUT transporter polypeptide.

5. A substantially pure DNA molecule encoding a GLUT transporter intracellular retention signal, the signal having an amino acid sequence of the formula (the sequence beginning with $A^1$ and ending with $A^{28}$ being represented by SEQ ID NO:10):

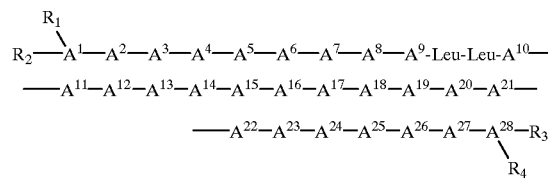

6. A vector comprising the DNA molecule of any one of claims 1, 2, 3, or 4 said vector directing the expression of the polypeptide encoded by said DNA molecule in a vector-containing cell.

7. A host cell comprising the DNA molecule of any one of claims 1, 2, 3, or 4.

* * * * *